US012740708B2

(12) United States Patent
Kim et al.

(10) Patent No.: US 12,740,708 B2
(45) Date of Patent: Sep. 22, 2026

(54) VIRTUAL HYPERSPECTRAL IMAGING OF BIOLOGICAL TISSUE FOR BLOOD HEMOGLOBIN ANALYSIS

(71) Applicant: Purdue Research Foundation, West Lafayette, IN (US)

(72) Inventors: Young L. Kim, West Lafayette, IN (US); Md Munirul Haque, Fishers, IN (US); Michelle Amaris Visbal-Onufrak, Las Piedras, PR (US); Sang Mok Park, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 1079 days.

(21) Appl. No.: 17/779,492

(22) PCT Filed: Nov. 24, 2020

(86) PCT No.: PCT/US2020/062016
§ 371 (c)(1),
(2) Date: May 24, 2022

(87) PCT Pub. No.: WO2021/118805
PCT Pub. Date: Jun. 17, 2021

(65) Prior Publication Data

US 2023/0000357 A1 Jan. 5, 2023

Related U.S. Application Data

(60) Provisional application No. 62/945,816, filed on Dec. 9, 2019, provisional application No. 62/945,808, filed on Dec. 9, 2019.

(51) Int. Cl.
*A61B 5/1455* (2006.01)
*A61B 5/00* (2006.01)
(Continued)

(52) U.S. Cl.
CPC ........ *A61B 5/0075* (2013.01); *A61B 5/14546* (2013.01); *A61B 5/1455* (2013.01);
(Continued)

(58) Field of Classification Search
None
See application file for complete search history.

(56) References Cited

U.S. PATENT DOCUMENTS

| | | | | |
|---|---|---|---|---|
| 2009/0326383 | A1 | 12/2009 | Barnes et al. | |
| 2011/0025864 | A1 * | 2/2011 | Ludwig .................. | H04N 25/76 348/E5.024 |

(Continued)

FOREIGN PATENT DOCUMENTS

| | | |
|---|---|---|
| WO | 2018047171 | 3/2018 |

OTHER PUBLICATIONS

Boldrini, Barbara & Kessler, Waltraud & Rebner, Karsten & Kessler, Rudolf. (2012). Hyperspectral Imaging: A Review of Best Practice, Performance and Pitfalls for in-line and on-line Applications. Journal of Near Infrared Spectroscopy. 20. 438-. 10.1255/jnirs. 1003. (Year: 2012).*

(Continued)

*Primary Examiner* — Jason M Sims
*Assistant Examiner* — Nelson Alexander Glover
(74) *Attorney, Agent, or Firm* — Piroozi-IP, LLC

(57) ABSTRACT

A system for generating hyperspectral imaging data for measuring biochemical compositions is disclosed which includes a spectral imaging device adapted to acquire one or more hyperspectral linescan images, an optical imaging device with a red-green-blue (RGB) sensor adapted to acquire an RGB dataset, a processor adapted to co-locate a plurality of pixels in the RGB dataset vs. a corresponding plurality of pixels of the one or more hyperspectral linescan datasets, establish a transformation matrix utilizing the
(Continued)

plurality of co-located pixels, apply the transformation matrix to the RGB dataset to thereby generate the hyperspectral dataset, and analyze the generated hyperspectral image dataset to determine the biochemical compositions.

16 Claims, 14 Drawing Sheets

(51) Int. Cl.
*A61B 5/145* (2006.01)
*G01N 21/31* (2006.01)

(52) U.S. Cl.
CPC .......... *A61B 5/6898* (2013.01); *A61B 5/7267* (2013.01); *G01N 21/31* (2013.01)

(56) References Cited

U.S. PATENT DOCUMENTS

| | | | | |
|---|---|---|---|---|
| 2014/0093147 | A1 | 4/2014 | Stewart et al. | |
| 2015/0015692 | A1 | 1/2015 | Smart | |
| 2017/0150903 | A1 | 6/2017 | Barnes et al. | |
| 2019/0164290 | A1* | 5/2019 | Wang | G06N 3/08 |
| 2019/0331590 | A1 | 10/2019 | Jin | |

OTHER PUBLICATIONS

Kim T, Kim JI, Visbal-Onufrak MA, Chapple C, Kim YL. Nonspectroscopic imaging for quantitative chlorophyll sensing. J Biomed Opt. Jan. 2016;21(1):16008. doi: 10.1117/1.JBO.21.1.016008. Pmid: 26790643. (Year: 2016).*

McMurdy JW, Jay GD, Suner S, Trespalacios FM, Crawford GP. Diffuse reflectance spectra of the palpebral conjunctiva and its utility as a noninvasive indicator of total hemoglobin. J Biomed Opt. Jan.-Feb. 2006;11(1):014019. doi: 10.1117/1.2167967. PMID: 16526896. (Year: 2006).*

Seung-Chul Yoon et al.,, "Hyperspectral imaging using a color camera and its application for pathogen detection," Proc. SPIE 9405, Image Processing: Machine Vision Applications VIII, 940506 (Mar. 13, 2015); https://doi.org/10.1117/12.2083137 (Year: 2015).*

Mcmurdy et al., "Photonics-based in vivo total hemoglobin monitoring and clinical relevance," J. Biophoton. 2, 277-287 (2009).

Kim et al., "Combined reflectance spectroscopy and stochastic modeling approach for noninvasive hemoglobin determination via palpebral conjunctiva," Physiol. Rep. 2, e00192 (2014).

Kim et al., "Toward laboratory blood test-comparable photometric assessments for anemia in veterinary hematology," J. Biomed. Opt. 21, 107001 (2016).

Collings et al., "Non-invasive detection of anaemia using digital photographs of the conjunctiva," PLOS One 11, e0153286 (2016).

Dimauro et al., "Detecting clinical signs of anaemia from digital images of the palpebral conjunctiva," IEEE Access 7, 113488 (2019).

Chen et al., "Modified Wiener estimation of diffuse reflectance spectra from RGB values by the synthesis of new colors for tissue measurements," J. Biomed. Opt. 17, 030501 (2012).

Nishidate et al., "Estimation of melanin and hemoglobin using spectral reflectance images reconstructed from a digital RGB image by the Wiener estimation method," Sensors 13, 7902-7915 (2013).

Yoshida et al., "Multispectral imaging of absorption and scattering properties of in vivo exposed rat brain using a digital red-green-blue camera," J. Biomed. Opt. 20, 051026 (2015).

Yoon et al., "Hyperspectral imaging using RGB color for foodborne pathogen detection," J. Electron. Imaging 24, 043008 (2015).

Saafin et al., "Compressed sensing super resolution of color images," in 24th European Signal Processing Conference, pp. 1563-1567, (2016).

Kim et al., "Data-driven imaging of tissue inflammation using RGB-based hyperspectral reconstruction toward personal monitoring of dermatologic health," Biomed. Opt. Express 8, 5282-5296 (2017).

Liang et al., "Optimized method for spectral reflectance reconstruction from camera responses," Opt. Express 25, 28273-28287 (2017).

Galliani et al., "Learned spectral super-resolution," arXiv:1703.09470 (2017).

Koundinya et al., "2D-3D CNN based architectures for spectral reconstruction from RGB images," in IEEE/CVF Conference on Computer Vision and Pattern Recognition Workshops, pp. 957-964, (2018).

Kaya et al., "Towards spectral estimation from a single RGB image in the wild," arXiv:1812.00805 (2018).

Arad et al., "Ntire 2018 challenge on spectral reconstruction from RGB images," in IEEE/CVF Conference on Computer Vision and Pattern Recognition Workshop, pp. 1042-1051, (2018).

Yan et al., "Accurate spectral superresolution from single RGB image using multi-scale CNN," in Pattern Recognition and Computer Vision, pp. 206-217, (Springer, 2018).

Signoroni et al., "Deep learning meets hyperspectral image analysis: a multidisciplinary review," J. Imaging 5, 52 (2019).

Gedalin et al., "DeepCubeNet: reconstruction of spectrally compressive sensed hyperspectral images with deep neural networks," Opt. Express 27, 35811-35822 (2019).

Hasan et al., "Clinical testing of hemechip in Nigeria for point-of-care screening of sickle cell disease," Blood 132, 1095 (2018).

Smart et al., "Simultaneous point-of-care detection of anemia and sickle cell disease in Tanzania: the rapid study," Ann. Hematol. 97, 239-246 (2018).

Dauvin et al., "Machine learning can accurately predict pre-admission baseline hemoglobin and creatinine in intensive care patients," NPJ Digit. Med. 2, 116 (2019).

Briggs et al., Where are we at with point-of-care testing in haematology? Br. J. Haematol. 158, 679-690 (2012).

Guo et al., "Smartphone dongle for simultaneous measurement of hemoglobin concentration and detection of HIV antibodies," Lab Chip 15, 3514-3520 (2015).

Jaggernath et al., "Diagnostic accuracy of the HemoCue HB 301, STATSite MHgb and URIT-12 point-of-care hemoglobin meters in a central laboratory and a community based clinic in Durban, South Africa," Plos One 11, 0152184 (2016).

Moore et al., "Evaluation of noninvasive hemoglobin measurements in trauma patients," Am. J. Surg. 206, 1041-1047 (2013).

Kim et al., "Accuracy of continuous noninvasive hemoglobin monitoring: a systematic review and meta-analysis," Anesth. Analg. 119, 332-346 (2014).

Hiscock et al., "Systematic review and meta-analysis of method comparison studies of masimo pulse co-oximeters (Radical-7 or Pronto-7) and HemoCue absorption spectrometers (B-hemoglobin or 201+) with laboratory haemoglobin estimation," Anaesth. Intensive Care 43, 341-350 (2015).

Wang et al., "Noninvasive hemoglobin measurement using unmodified smartphone camera and white flash," in 39th Annual International Conference of the IEEE Engineering in Medicine and Biology Society, pp. 2333-2336, (2017).

Mannino et al., "Smartphone app for non-invasive detection of anemia using only patient-sourced photos," Nat. Commun. 9, 4924 (2018).

Sheth et al., , "The relation of conjunctival pallor to the presence of anemia," J. Gen. Intern. Med. 12, 102-106 (1997).

Shulman et al., "Screening for severe anaemia in pregnancy in Kenya, using pallor examination and self-reported morbidity," Trans. R. Soc. Trop. Med. Hyg. 95, 250-255 (2001).

Kalantri et al., "Accuracy and reliability of pallor for detecting anaemia: a hospital-based diagnostic accuracy study," PLOS One 5, e8545 (2010).

Lima et al., "Noninvasive monitoring of peripheral perfusion," Intensive Care Med. 31, 1316-1326 (2005).

Abraham et al., "Continuous monitoring of tissue pH with a fiberoptic conjunctival sensor," Ann. Emerg. Med. 14, 840-844 (1985).

(56) References Cited

OTHER PUBLICATIONS

Kent et al., Conjunctival vasculature in the assessment of anemia, Ophthalmology 107, 274-277 (2000).
Khansari et al., "Inter-visit variability of conjunctival microvascular hemodynamic measurements in healthy and diabetic retinopathy subjects," Microvasc. Res. 118, 7-11 (2018).
Suner et al., "Non-invasive determination of hemoglobin by digital photography of palpebral conjunctiva," J. Emerg. Med. 33, 105-111 (2007).
Gwn Lore et al., "Generative adversarial networks for spectral super-resolution and bidirectional RGB-to-multispectral mapping," in IEEE Conference on Computer Vision and Pattern RecognitionWorkshops (2019).
Liu et al., "Deep learning-based color holographic microscopy," J. Biophoton. 12, e201900107 (2019).
Edwards et al., "Smartphone based optical spectrometer for diffusive reflectance spectroscopic measurement of hemoglobin." Scientific reports 7.1: 1-7, (2017).
Kim et al., "Comparison of the accuracy of noninvasive hemoglobin sensor (NBM-200) and portable hemoglobinometer (HemoCue) with an automated hematology analyzer (LH500) in blood donor screening." Annals of laboratory medicine 33.4: 261 (2013).
Avcioglu et al., "Comparison of noninvasive and invasive point-of-care testing methods with reference method for hemoglobin measurement." Journal of clinical laboratory analysis 32.3: e22309 (2018).
Kavsaoğlu et al., "Non-invasive prediction of hemoglobin level using machine learning techniques with the PPG signal's characteristics features." Applied Soft Computing 37: 983-991 (2015).
Lamhaut et al., "Comparison of the accuracy of noninvasive hemoglobin monitoring by spectrophotometry (SpHb) and HemoCue® with automated laboratory hemoglobin measurement." The Journal of the American Society of Anesthesiologists 115.3: 548-554 (2011).
Li et al., "Noninvasive hemoglobin measurement based on optimizing Dynamic Spectrum method." Spectroscopy etters 50.3: 164-170 (2017).
Liu et al., "Development and validation of a photoplethysmography system for noninvasive monitoring of hemoglobin concentration." Journal of Electrical and Computer Engineering (exact date in 2020 unknown).
Timm et al., "Novel multi wavelength sensor concept to detect total hemoglobin concentration, methemoglobin and oxygen saturation." Optical Diagnostics and Sensing XV: Toward Point-of-Care Diagnostics. vol. 9332. SPIE, 2015.
Wang et al., "HemaApp: noninvasive blood screening of hemoglobin using smartphone cameras." Proceedings of the 2016 ACM International Joint Conference on Pervasive and Ubiquitous Computing. 2016.
Park et al., "mHealth spectroscopy of blood hemoglobin with spectral super-resolution," Optica 7:563, 2020.
ISR of PCT/US20/62016, 2021.

* cited by examiner

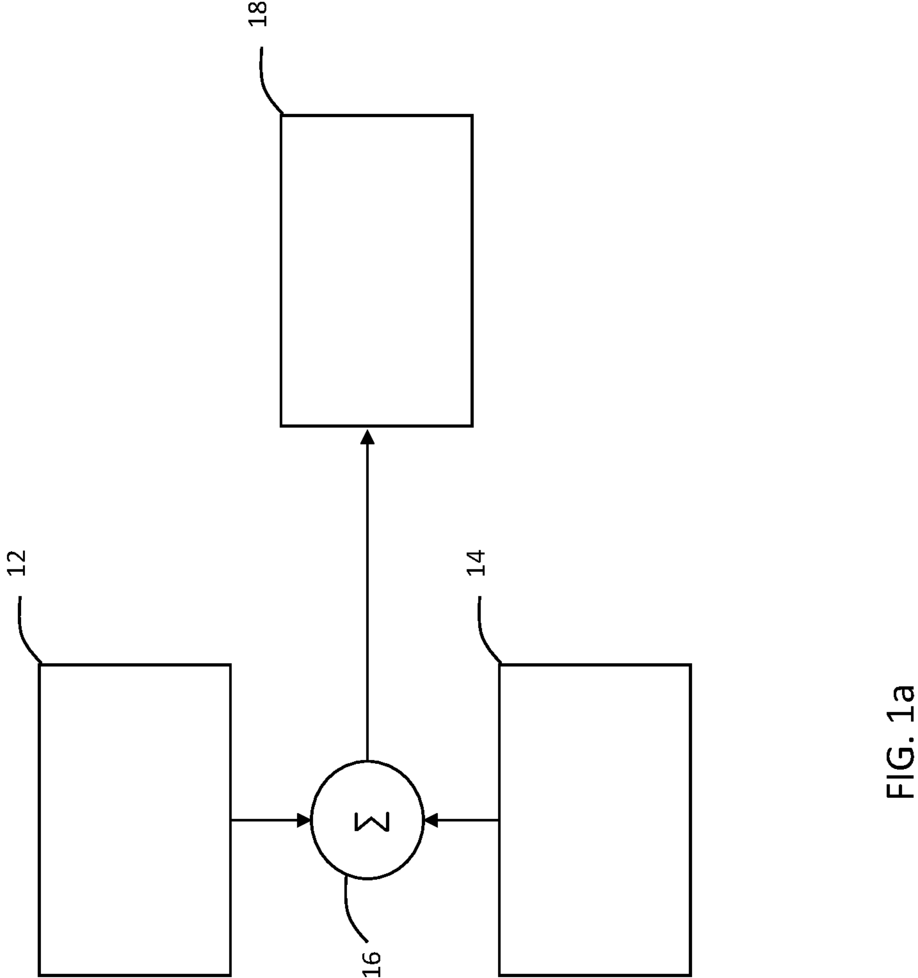
FIG. 1a

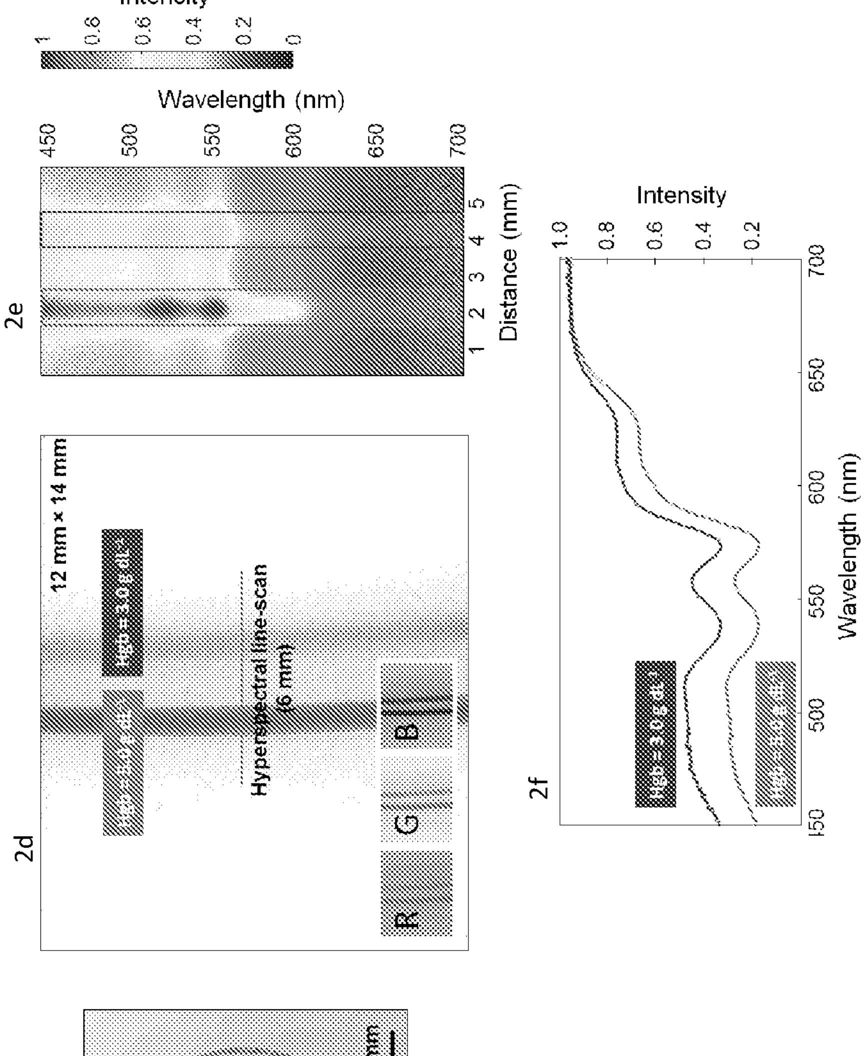
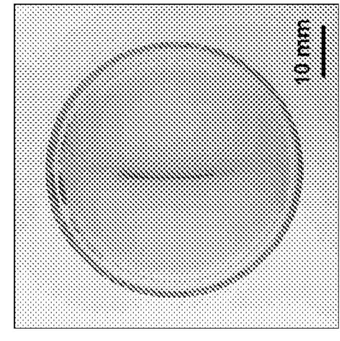
FIGs. 2c, 2d, 2e, and 2f

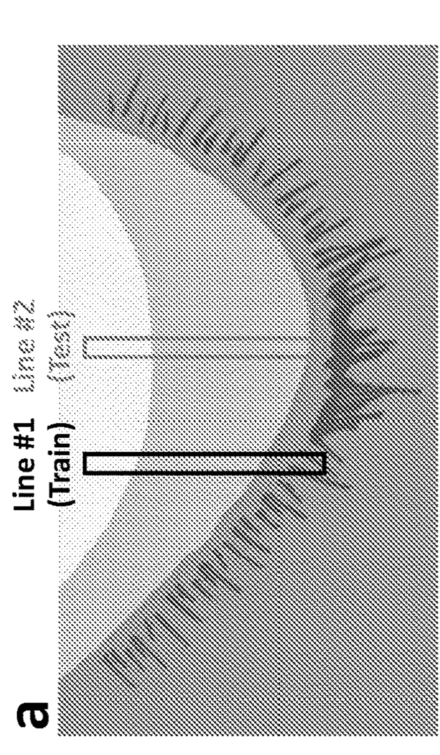
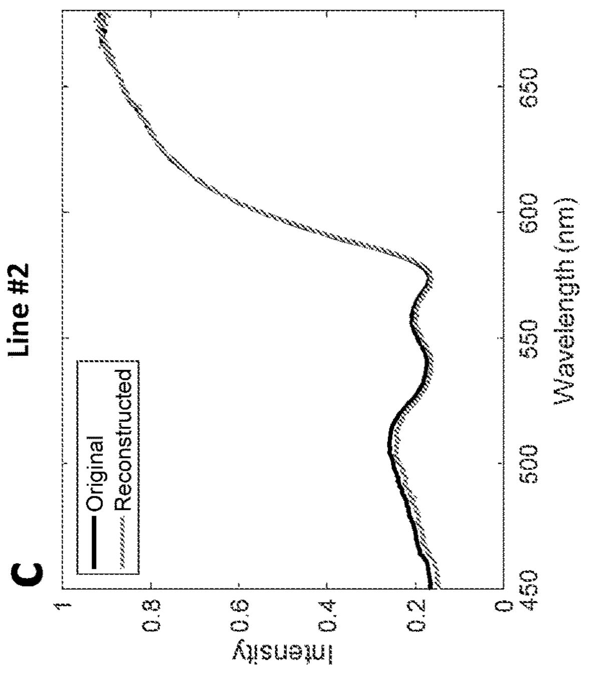
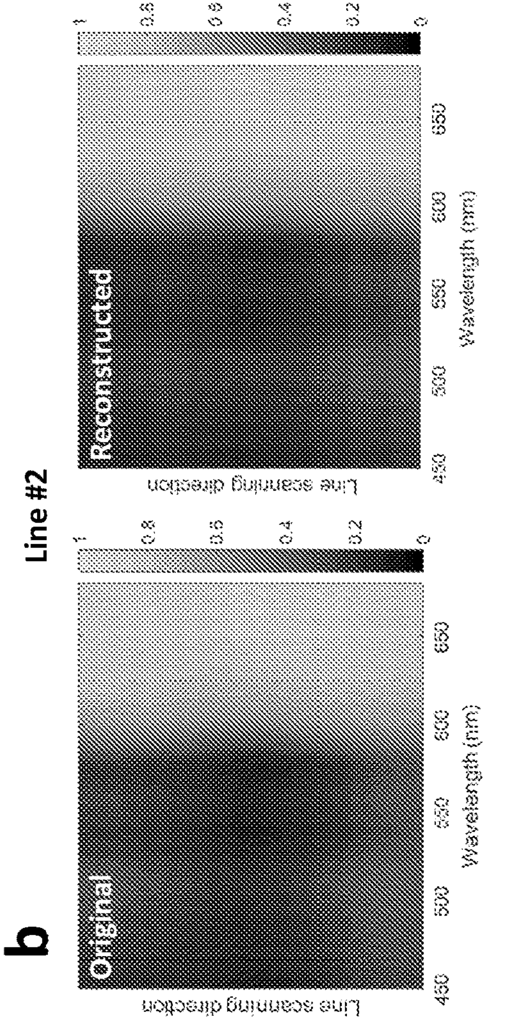
FIG. 5a, 5b, and 5c

VIRTUAL HYPERSPECTRAL IMAGING OF BIOLOGICAL TISSUE FOR BLOOD HEMOGLOBIN ANALYSIS

CROSS-REFERENCE TO RELATED APPLICATIONS

The present patent application is a 35 U.S.C. § 371 Nationalization Application of and claims the priority benefit of the International Patent Application Serial No. PCT/US20/62016 filed Nov. 24, 2020, which is related to and claims the priority benefit of U.S. Provisional Patent Application Ser. No. 62/945,808 filed Dec. 9, 2019, titled "VIRTUAL HYPERSPECTRAL IMAGING OF BIOLOGICAL TISSUE FOR BLOOD HEMOGLOBIN ANALYSIS"; and U.S. Provisional Patent Application Ser. No. 62/945,816, filed Dec. 9, 2019, titled "HYPERSPECTRAL IMAGE CONSTRUCTION OF BIOLOGICAL TISSUE FOR BLOOD HEMOGLOBIN ANALYSIS USING A SMARTPHONE" the contents of each of which are hereby incorporated by reference in its entirety into the present disclosure.

STATEMENT REGARDING GOVERNMENT FUNDING

This invention was made with government support under R21TW010620 awarded by the National Institutes of Health and 7200AA18CA00019 awarded by the US Agency for International Development. The government has certain rights in the invention.

TECHNICAL FIELD

The present disclosure generally relates to generating a hyperspectral imaging dataset, recovering hyperspectral information from RGB values, analyzing blood, and in particular, to a system and method of analyzing biological tissue for blood hemoglobin analysis.

BACKGROUND

This section introduces aspects that may help facilitate a better understanding of the disclosure. Accordingly, these statements are to be read in this light and are not to be understood as admissions about what is or is not prior art.

Blood hemoglobin (Hgb) tests are routinely ordered as an initial screening of the amount of red blood cells (or hemoglobin) in the blood as part of a general health test for a subject. Blood Hgb tests are extensively performed for a variety of patient care needs, such as anemia detection as a cause of other underlying diseases, hemorrhage detection after traumatic injury, assessment of hematologic disorders, and for transfusion initiation. There are several biological assays for measuring blood Hgb content in grams per deciliter (i.e. g $dL^{-1}$) from blood drawn via traditional needle-based methods. Portable point-of-care hematology analyzers using blood draws (e.g. Abbott i-STAT and HemoCue) are also commercially available. However, all these tests require expensive and environment-sensitive analytical cartridges with short shelf lives, as well as unaffordable for both resource-limited and homecare settings. In addition, repeated blood Hgb measurements using these invasive tests can cause iatrogenic complications such as blood loss.

Unlike measuring oxygen saturation with pulse oximetry, noninvasive measurements of a total Hgb concentration in the blood are not straightforward. A few noninvasive Hgb testing devices (e.g. MASIMO and ORSENSE) have recently become available that are currently undergoing clinical studies for immediate reading and continuous monitoring of blood Hgb levels in different clinical settings. Aside from the relatively high cost associated with operating and maintaining the equipment, the medical community agrees that the broad limits of agreement between these devices and central laboratory tests pose a significant challenge in making clinical decision, thus generating skepticism in clinical adaptation. Several smartphone-based anemia detection technologies (e.g., HEMOGLOBE, EYENAEMIA, AND HEMAAPP) have also made progress, however, most of these mobile applications are intended for initial screening or risk stratification of severe anemia and are not developed for measuring exact Hgb content in the unit of g $dL^{-1}$.

Therefore, there is an unmet need for a novel technology that can provide non-invasive Hgb measurements that can be relied for accuracy without the complications associated with expensive laboratory equipment.

SUMMARY

A system for generating hyperspectral imaging data for measuring biochemical compositions is disclosed. The system includes a spectral imaging device adapted to acquire one or more hyperspectral linescan images from one or more regions of interest of a subject, thereby generating one or more hyperspectral linescan datasets. The system further includes an optical imaging device with a red-green-blue (RGB) sensor adapted to acquire an RGB image from the region of interest of the subject, thereby generating an RGB dataset. The system further includes a processor which is adapted to co-locate a plurality of pixels in the RGB dataset vs. a corresponding plurality of pixels of the one or more hyperspectral linescan datasets. The processor is further adapted to establish a transformation matrix utilizing the plurality of co-located pixels, the transformation matrix adapted to convert the RGB dataset into a hyperspectral dataset of the region of interest. Additionally, the processor is adapted to apply the transformation matrix to the RGB dataset to thereby generate the hyperspectral dataset for the region of interest. Furthermore, the processor is adapted to analyze the generated hyperspectral image dataset to determine the biochemical compositions.

According to one embodiment, in the system of the present disclosure each of the plurality of co-located pixels from the RGB dataset is associated with a 3×1 RGB value matrix.

According to one embodiment, in the system of the present disclosure each of the co-located plurality of pixels from the hyperspectral linescan dataset is associated with an N×1 spectrum matrix, where N represents discretized spectra between a lower bound and an upper bound.

According to one embodiment, in the system of the present disclosure the lower and upper bounds are determined by the spectral range of RGB sensors.

According to one embodiment, in the system of the present disclosure the spectral range of sensors are between 400 nm and 800 nm.

According to one embodiment, in the system of the present disclosure the transformation matrix is an inverse of the RGB response function matrix of the RGB sensor.

According to one embodiment, in the system of the present disclosure the inverse of the transformation matrix is determined numerically by using RGB and spectral data from a subset of the collocated plurality of pixels.

According to one embodiment, in the system of the present disclosure the region of interest includes inner eyelid.

According to one embodiment, in the system of the present disclosure the biochemical compositions includes blood hemoglobin.

According to one embodiment, in the system of the present disclosure the biochemical compositions are determined using spectral analysis.

According to one embodiment, in the system of the present disclosure the spectral analysis includes a partial least square regression statistical modeling technique to first build a model from a training set of a first hyperspectral dataset vs. the biochemical compositions and then apply the model to a second dataset from the generated hyperspectral image dataset.

A method for generating hyperspectral imaging data for measuring biochemical compositions is also disclosed. The method includes obtaining one or more hyperspectral linescan images using a spectral imaging device from one or more region of interest of a subject, thereby generating one or more hyperspectral linescan datasets. The method also includes obtaining an RGB image from the region of interest using an optical imaging device with a red-green-blue (RGB) sensor, thereby generating an RGB dataset. The method further includes co-locating a plurality of pixels in the RGB dataset vs. a corresponding plurality of pixels of the one or more hyperspectral linescan datasets. Additionally, the method includes establishing a transformation matrix utilizing the plurality of co-located pixels, the transformation matrix adapted to convert the RGB dataset into a hyperspectral dataset of the region of interest. Furthermore, the method includes applying the transformation matrix to the RGB dataset to thereby generate the hyperspectral dataset for the region of interest. The method also includes analyzing the generated hyperspectral image dataset to determine the biochemical compositions.

According to one embodiment, in the method of the present disclosure each of the plurality of co-located pixels from the RGB dataset is associated with a 3×1 RGB value matrix.

According to one embodiment, in the method of the present disclosure each of the co-located plurality of pixels from the hyperspectral linescan dataset is associated with an N×1 spectrum matrix, where N represents discretized spectra between a lower bound and an upper bound.

According to one embodiment, in the method of the present disclosure the lower and upper bounds are determined by the spectral range of RGB sensors.

According to one embodiment, in the method of the present disclosure the spectral range of sensors are between 400 nm and 800 nm.

According to one embodiment, in the method of the present disclosure the transformation matrix is an inverse of the RGB response function matrix of the RGB sensor.

According to one embodiment, in the method of the present disclosure the inverse of the transformation matrix is determined numerically by using RGB and spectral data from a subset of the co-located plurality of pixels.

According to one embodiment, in the method of the present disclosure the region of interest includes inner eyelid.

According to one embodiment, in the method of the present disclosure the biochemical compositions are determined using spectral analysis.

According to one embodiment, in the method of the present disclosure the spectral analysis includes a partial least square regression statistical modeling technique to first build a model from a training set of a first hyperspectral dataset vs. the biochemical compositions and then apply the model to a second dataset from the generated hyperspectral image dataset.

BRIEF DESCRIPTION OF DRAWINGS

FIG. 1*a* is a simplified block diagram depicting the major blocks of the system of the present disclosure.

FIG. 2*c* is a photograph of the microvessel-mimicking phantom.

FIGS. 2*d* and 2*e* are hyperspectral linescans are shown outlined in the RGB image of the microvessel phantom of FIG. 2*c*.

FIG. 2*f* spectra are shown corresponding to the average intensity along the distance outline in FIG. 2*e* for two different Hgb concentrations.

FIG. 5*a* is a schematic of an inner eyelid showing a first linescan (line 1) used for training a model and a second line scan (line 2) for testing the model.

FIGS. 5*b* and 5*c* are blood hemoglobin (HGb) in g dL-1 vs. wavelength in nm (FIG. 5*b*) and intensity vs. wavelength in nm for an obtained hyperspectral dataset vs. a calculated hyperspectral dataset (i.e., line 1 vs. line 2 of FIG. 5*a*) according to the algorithm of the present disclosure.

DETAILED DESCRIPTION

Figure 1B:
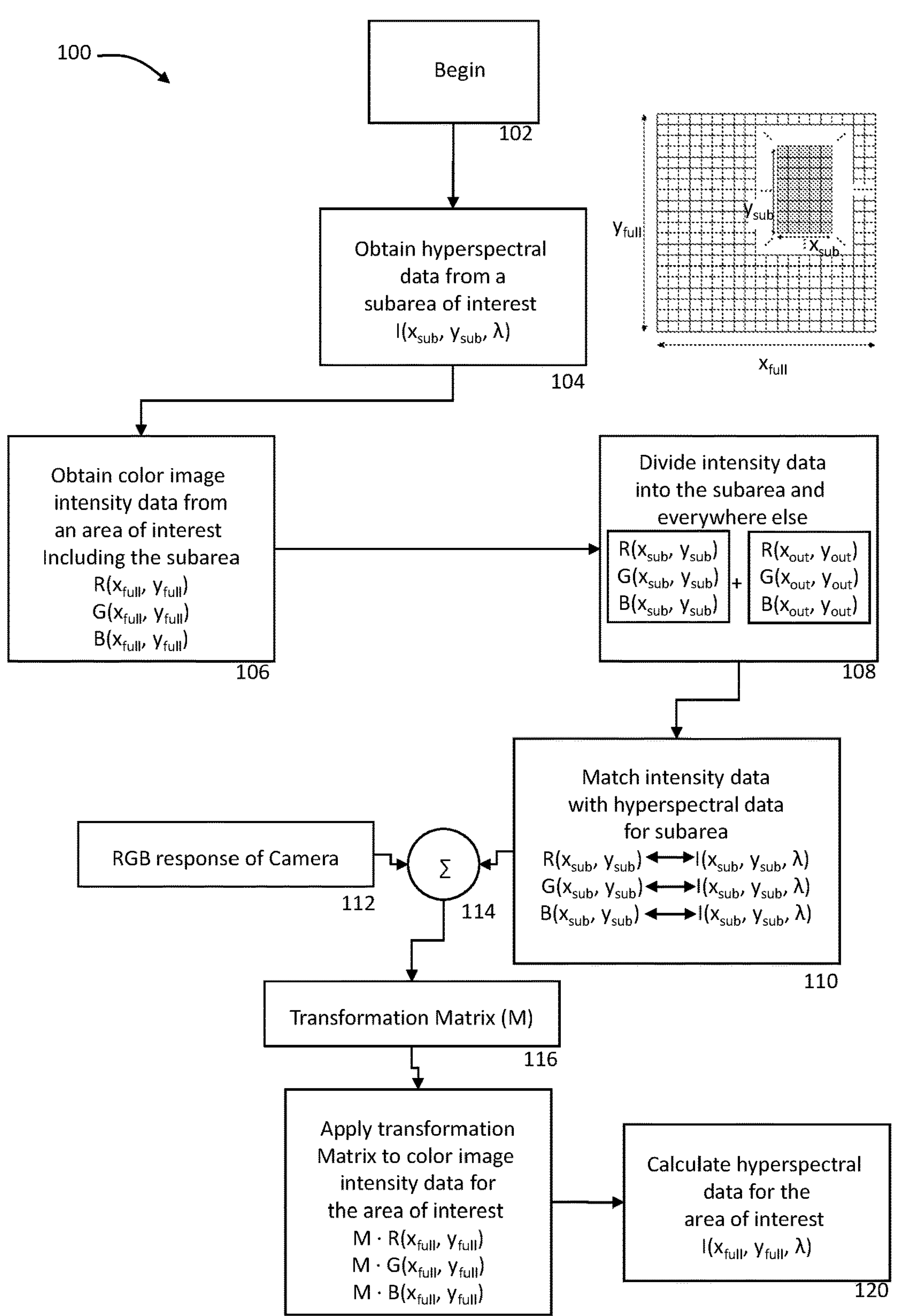
FIG. 1*b* a flowchart of steps of an algorithm of the present disclosure is provided.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In the present disclosure, the term "about" can allow for a degree of variability in a value or range, for example, within 10%, within 5%, or within 1% of a stated value or of a stated limit of a range.

In the present disclosure, the term "substantially" can allow for a degree of variability in a value or range, for example, within 90%, within 95%, or within 99% of a stated value or of a stated limit of a range.

For noninvasive blood Hgb measurements, it is important to rely on an appropriate anatomical sensing site where the underlying microvasculature is exposed on the skin surface without being affected by confounding factors of skin pigmentation and light absorption of molecules (e.g. melanin) in tissue. Commonly used clinical examination sites of pallor or microcirculation, such as the conjunctiva, the nailbed, the palm, and the sublingual region, provide a clue for an examination site selection. Specially, the palpebral conjunctiva (i.e. inner eyelid) can serve as an ideal site for peripheral access, because the microvasculature is easily visible and melanocytes are absent. The easy accessibility of the inner eyelid allows for reflectance spectroscopy and digital photography to be tested for anemia assessments.

To this end, the present disclosure advantageously applies techniques typically used in astrophysics to the inside of the eyelid to ascertain hyperspectral imaging data of tissue which can then be used to measure effective blood hemoglobin content. Referring to FIGS. 1*a*, 1*b*, 1*c*, and 1*d*, a block diagram and flowcharts depicting the system and method of the present disclosure are provided. Referring to FIG. 1*a*, a simplified block diagram is shown depicting the major blocks of the system 10 of the present disclosure. The system 10 includes a hyperspectral imaging system that can associate wavelength from a plurality of pixels. It should be appreciated that hyperspectral imaging of a large area represents complex imaging equipment and complex processes; however, producing a linescan, as discussed below, is significantly more straightforward and simplified. A linescan, however, cannot generate the information on the entire area of interest needed to calculate the target output which is a measure of hemoglobin. Referring to FIG. 1*a*, the system 10 includes a linescan imaging apparatus 12 capable of generating linescans of a subarea of an area of interest, and a color (RGB) imaging apparatus 14 capable of generating a red-green-blue (RGB) image of the entire area of interest. The output of these two imaging apparatuses are combined by a processing system (not shown) but partially represented as a summer 16 which produces a matrix of intensity as a function of the position (x, y) and the wavelength of light $\lambda$ (also known as a hypercube or a hyperspectral image) without using a conventional hyperspectral imaging system. Using a hyperspectral dataset and an RGB dataset from the subarea (or a line), a transformation (or extrapolation) algorithm (referred to herein as a virtual hyperspectral imaging (VHI) algorithm depicted across FIGS. 1*b*, 1*c*, and 1*d*) is used to construct a hyperspectral image for the larger area of interest, all of which is represented by the summer 16. The aforementioned transformation algorithm is then applied to the RGB dataset at pixels outside the subarea (or line) to generate a hyperspectral image dataset for the entire area by the processing system (not shown), as represented by the block 18.

Referring to FIG. 1*b*, the specifics of VHI algorithm is provided, as provided herein. First, a method 100 is described performed by the processing system (not shown). The Method 100 begins at the initial block 102 (identified as "Begin"). The method 100 then proceeds to a block 104 wherein the method 100 obtains a hyperspectral linescan data from the linescan imaging apparatus 12 (see FIG. 1*a*) of a subarea (or line) of interest. The output of the linescan is provided as $I(x_{sub}, y_{sub}, \lambda)$ for each pixel in the subarea (or line), where $\lambda$ is the wavelength output of the pixel having location x and y. The method 100 next move to a block 106 where an RGB image from the area of interest is obtained from the RGB imaging apparatus 14. The data obtained includes three image intensity sets: one for Red ($R(x_{full}, y_{full})$), one for Green ($G(x_{full}, y_{full})$), and one for Blue ($B(x_{full}, y_{full})$). Next the method 100 proceeds to a block 108 where the image intensity sets of the block 106 are divided into the subarea (or line) and everywhere else. The subarea image intensity dataset includes: $R(x_{sub}, y_{sub})$, $G(x_{sub}, y_{sub})$, and $B(x_{sub}, y_{sub})$; and $R(x_{out}, y_{out})$, $G(x_{out}, y_{out})$, and $B(x_{out}, y_{out})$, where sub≠out. Next, the method 100 proceeds to a block 110 where the hyperspectral datasets from the block 104 matched to the RGB image intensity data of the subarea (or line) from the block 108. In particular, the method 100 makes the following correspondences: $R(x_{sub}, y_{sub}) \longleftrightarrow I(x_{sub}, y_{sub}, \lambda)$, $G(x_{sub}, y_{sub}) \longleftrightarrow I(x_{sub}, y_{sub}, \lambda)$, and $B(x_{sub}, y_{sub}) \longleftrightarrow I(x_{sub}, y_{sub}, \lambda)$. The method 100 then obtains the RGB spectral response functions (also known as RGB spectral sensitivity functions) of the RGB imaging apparatus 14 (see FIG. 1*a*), as shown in a block 112. The RGB spectral response functions of the RGB imaging apparatus is data that is provided by the manufacturer of the RGB imaging apparatus (sensors and cameras) 14 (see FIG. 1*a*). The datasets in the blocks 112 and 110 are combined as provided by the summer 114, in order to generate a transformation matrix (M) in a block 116, according to a procedure provided in FIG. 1*d*, discussed below. Once the transformation matrix is generated in the block 116, the method 100 applies the transformation matrix to the image intensity data of the area of interest as provided in a block 118. This operation is defined by the operation: $M \cdot R(x_{full}, y_{full})$, $M \cdot G(x_{full}, y_{full})$, and $M \cdot B(x_{full}, y_{full})$. The operation in the block 118 results in the hyperspectral data for the area of interest $I(x_{full}, y_{full}, \lambda)$ as provided in a block 120.

Figure 1C:
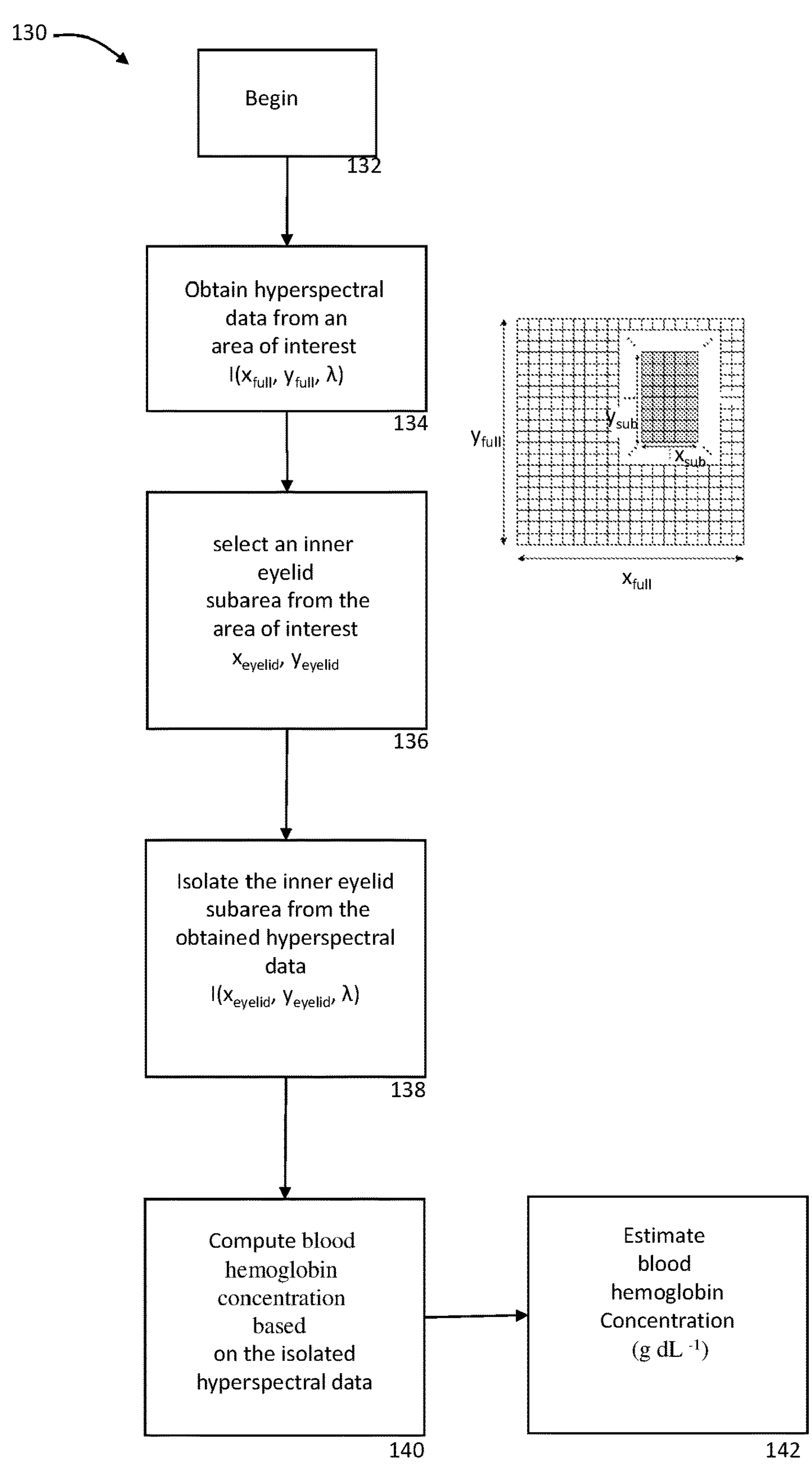
FIG. 1*c* a flowchart of steps of an algorithm of the present disclosure is provided.

Referring to FIG. 1*c*, a method 130 is shown that uses the hyperspectral data of the area of interest (i.e., the output of the method 100 as provided in the block 120 (see FIG. 1*b*)) and applies that output to obtain an estimate of hemoglobin. The method 130 starts in a block 132 (identified as "Begin"). The method then proceeds to a block 134 where the output of the block 120 (see FIG. 1*b*) is obtained. Next an area of the eyelid is isolated ($x_{eyelid}, y_{eyelid}$) as provided in a block 136 and the hyperspectral data from this area is separated from the larger area of interest. This output is shown in a block 138 as $I(x_{eyelid}, y_{eyelid}, \lambda)$. Next the method 130 computes the hemoglobin concentration based on the isolated hyperspectral data output of the block 138, as provided in a block 140. The method 130 then proceeds to a block 142 where the estimate of the hemoglobin concentration ($gdL^{-1}$) is provided as the output of the method 130.

Figure 1D:
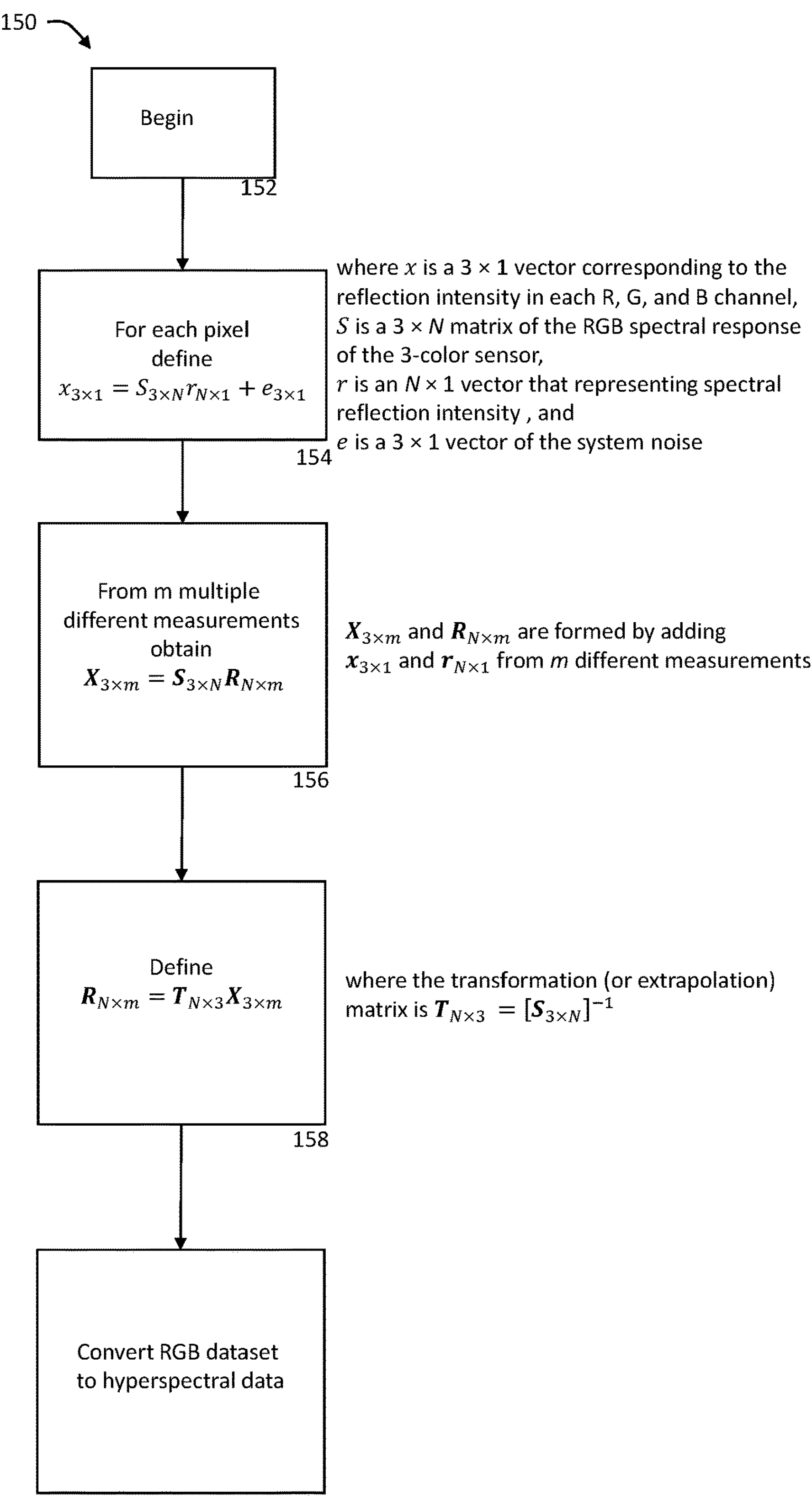
FIG. 1*d* a flowchart of steps of an algorithm of the present disclosure is provided.

Referring to FIG. 1*d*, a method 150 according to the present disclosure is provided to depict how the transformation matrix (M), see block 116 of FIG. 1*b*, is generated. The method 150 begins at a block 152 (identified as "Begin"). The steps of the method 150 are described below.

Figure 2A:
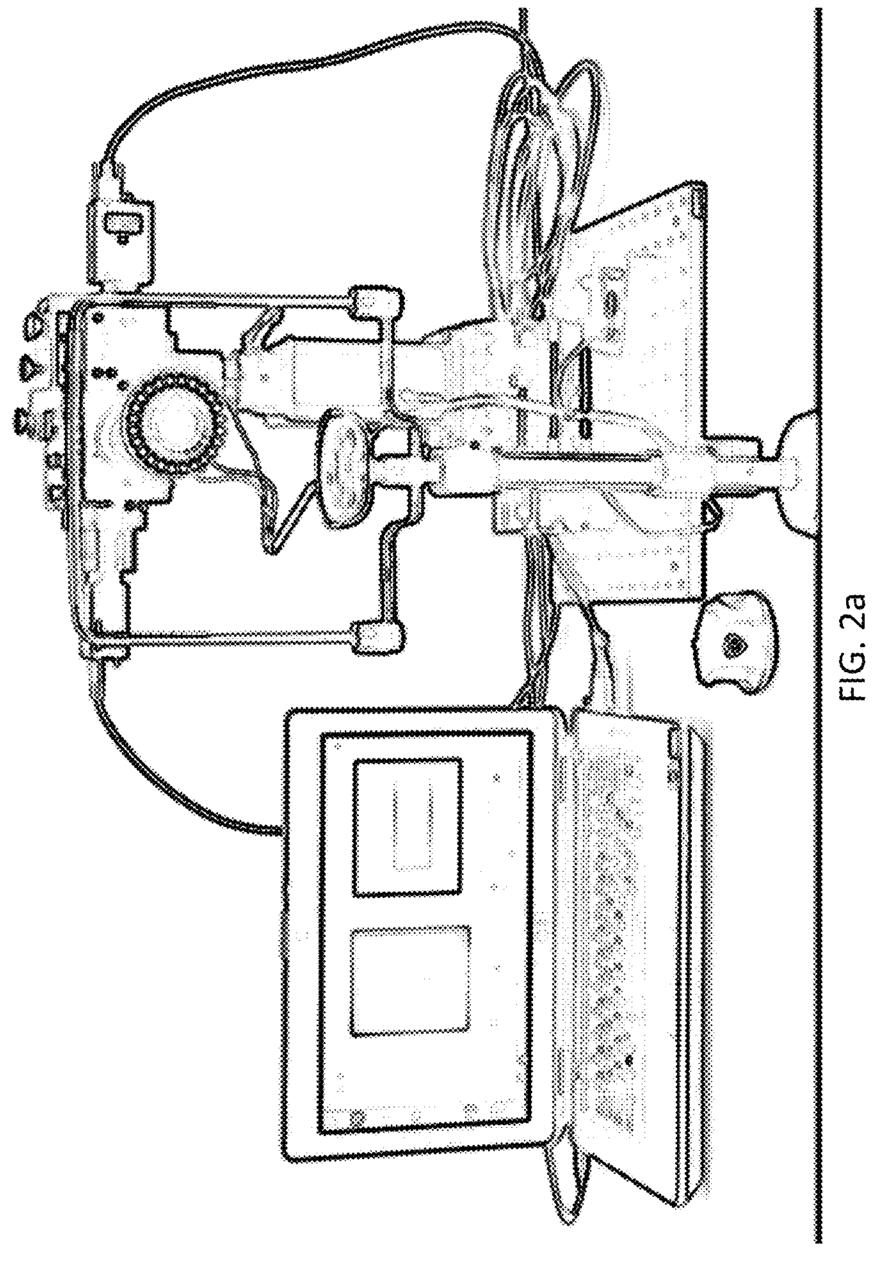
FIGS. 2*a* and 2*b* provide a photograph of a hyper-spectrographic setup capable of providing a hyperspectral image data for a subarea (or a line) as shown in FIG. 2*b*.
Figure 2B:
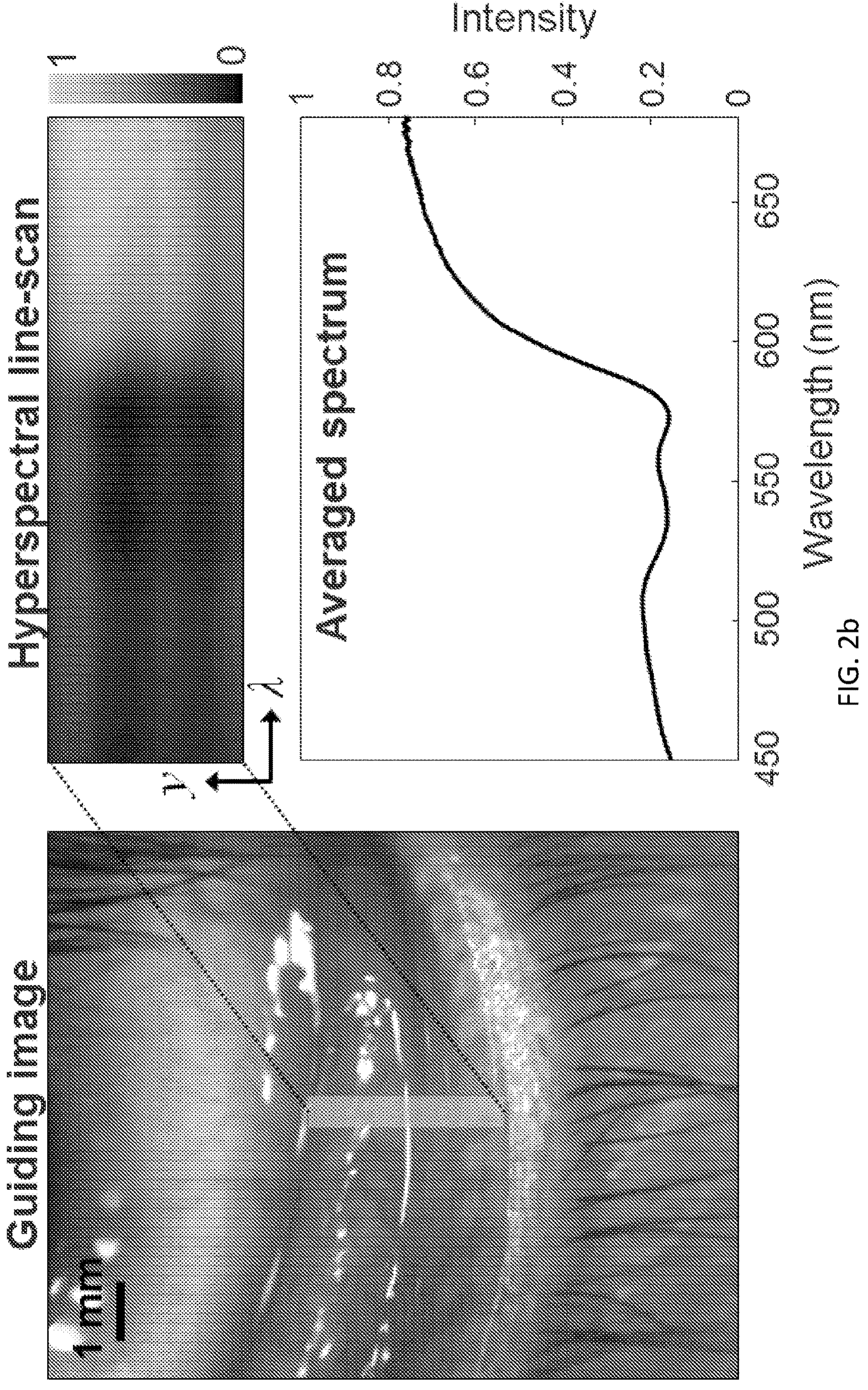

Referring to FIGS. 2*a* and 2*b*, a photograph of a hyperspectrographic setup is shown capable of providing a hyperspectral image data for a subarea (or a line). The system shown in FIG. 2*a* includes a dual-channel system in which one detection arm is coupled with a hyperspectral linescanning system (see linsescan imaging apparatus 12 of FIG. 1*a*) and the other detection arm is coupled with an imaging camera with an RGB imaging sensor (see RGB imaging apparatus of FIG. 1*b*). The setup shown in FIG. 2*a* is inspired by an astronomical hyperspectral imaging system, which is used for imaging the inner eyelid. A subject sits in front of the system, facing a telecentric lens (or a lens), places the chin on the chinrest, and pulls down the eyelid for imaging when instructed. The system is adapted to instantaneously acquire a hyperspectral line in the center of the inner eyelid. The RGB image also shows the exact location where the hyperspectral linescanning is performed (shown as a translucent white rectangle with a physical height of about 6.4 mm). The hyperspectral linescan dataset contains spatial (y), which serves as a subarea and wavelength (λ) information. When the averaged spectrum corresponds to the average intensity along the spatial y axis for each λ value, the characteristic absorption of hemoglobin (Hgb) is clearly visible. As a result, a two-dimensional hyperspectral graph of y vs. λ is generated, shown adjacent the photograph of an example inner eyelid, provided in FIG. 2*b*, for the hyperspectral linescan dataset. This two-dimensional graph can then be represented as a graph of wavelength in nm vs. intensity, also shown in FIG. 2*b* and aligned with the two-dimensional hyperspectral graph of y vs. λ.

Referring back to FIG. 2*a*, this custom-built dual-channel system shown uses a dual-channel spectrograph (Shelyak Instruments) that has two detection arms to allows for simultaneous acquisitions of hyperspectral and RGB image data along the line. To provide broadband white-light illumination to the inner eyelid, a white-light LED ring (Neopixel RGBW 24 LED ring, Adafruit Industries) is attached to a telecentric lens (0.5×, Edmund Optics) via a custom-built 3-D printed ring holder to fit the lens circumference. Other lenses can be used, however, a telecentric lens offers the ability to eliminate parallax error and to provide constant magnification. Telecentric imaging is also beneficial for biological tissue, including resolution enhancement by diffuse light suppression, large constant transverse field of view, consistent magnification over the axial direction, and long working distance. The intensity of the LED ring is controlled with a microcontroller (Arduino UNO). The image-guided hyperspectral linescanning system has two data acquisition ports: hyperspectral line-scanning port mounted with a mono CCD camera (e.g., PointGrey Grasshopper3 5.0 MP Mono, FUR Integrated Imaging Solutions Inc.) and image port mounted with a 3-color CCD (e.g., PointGrey Grasshopper3 5.0 MP Color). For hyperspectral linescanning (length=6.4 mm), the telecentric lens collects light scattered from the inner eyelid, which passes through the slit of the spectrograph and disperses with a diffraction grating. The diffraction grating in the dual-channel spectrograph was selected to cover the visible wavelength range of 400-700 nm and the slitwidth is 23 μm inside the system, resulting in a spectral resolution of Δλ=1 nm as shown in FIG. 2*b*. For RGB imaging, the light from the inner eyelid is reflected via another mirror toward the imaging port to generate a field of view (14 mm×12 mm) with a spatial resolution of ~150 μm. It should be noted that by changing the imaging lens, the field of view can easily be increased for other applications. The custom-built dual-channel system rests on a base with two interlocked x-y-z positioning bases that serve to move the imaging system to locate the eyelid image centered within the rectangular region of interest (ROI), also referred to herein as the area of interest, guide. A LabVIEW Virtual Instrument (National Instruments Corporation) was generated to synchronize data acquisition, LED light control, and background room light subtraction. A series of tests were conducted using tissue-mimicking phantoms, see FIGS. 2*c*, 2*d*, 2*e*, and 2*f*. In FIG. 2*c* a photograph of the microvessel-mimicking phantom is presented. Hgb-filled tubings are fixed at the bottom of the glass petri dish and are submerged in the optical scattering suspension. In FIGS. 2*d* and 2*e*, a hyperspectral linescan is outlined in the RGB image of the microvessel phantom. The microvessels are positioned perpendicular to the linescan. In FIG. 2*f*, each spectrum shown corresponds to the average intensity along the distance outline in FIG. 2*e*. The microvessel with a higher Hgb concentration (5.0 g dL-1) has a lower reflection intensity for the wavelengths between 450 and 550 nm than the lower Hgb concentration (3.0 g dL-1). During eyelid imaging, the subject is asked to sit down facing the imaging system and to place their head in a chinrest. Once the eyelid is correctly focused and positioned within the ROI rectangle, we proceed with data acquisition, while reminding the individual the instructions not to move or close their eyes until the completion of imaging session. Measurements of a reference reflectance standard (SRT-99-050, Labsphere, Inc.) are also conducted with the hyperspectral line-scanning system to correct for the system response (both illumination and detection).

As discussed above, a single hyperspectral linescan dataset, however, does not have sufficient information to reliably use for hemoglobin data extraction from the entire inner eyelid. Therefore, what is needed is additional hyperspectral data for the entire inner eyelid that can be used for averaging and other statistical operations. Such additional data can be formed from additional linescans or based on extrapolation of one or more linescans, see FIGS. 1*a*, 1*b*, and 1*c*. According to one embodiment of the present disclosure, a sufficient number of hyperspectral linescan datasets can be progressively scanned and generated and then stitched together to form an ensemble of a portion of the inner eyelid. This is a typical approach of conventional hyperspectral imaging systems. Such a process is cumbersome and very slow for hyperspectral data acquisition, since it will require accounting for slight movement of the subject during each linescan capture. Alternatively, the linescan dataset can be used as a baseline and the same extrapolated using an RGB image whereby the RGB image is converted into a hyperspectral graph based on the single or multiple hyperspectral linescan datasets, as discussed above and with reference to the present disclosure. For example, in the latter approach, one or more hyperspectral linescan datasets or hyperspectral data for the entire area can be generated. In other words, the hyperspectral data and the RGB image from the line is used to construct a transformation matrix (M, see block 116 in FIG. 1*b*) that mathematically predicts a hyperspectrum from the RGB data at a pixel location outside the line. One hyperspectral linescan dataset and its corresponding RGB dataset are sufficient to construct the transformation matrix. By applying this transformation matrix to all of the pixel locations outside the line, a hyperspectral imaging dataset is generated for the entire area (see block 120 in FIG. 1*b*). This extrapolation approach is referred to herein as the virtual hyperspectral imaging (VHI) algorithm/system. The VHI approach advantageously requires only one raw hyperspectral linescan dataset and an RGB image at the minimum, preferably produced at the same time to avoid subject movement, simplifying the imaging requirements, significantly. The custom-built dual channel system shown in FIG. 2*a*, allows simultaneous acquisitions of hyperspectral line-scanning and RGB imaging. It should be noted that the hyperspectral image(s) and the RGB image can be produced at different times in close proximity to one another, as long as any variations due to movement of the eyelid is considered. With the VHI approach, a hyperspectral dataset for the entire eyelid can be generated in order to form a more accurate correlation to hemoglobin with only one or more hyperspectral linescan datasets and an RGB image.

The spectroscopic and VHI blood Hgb measurements systems and methods of the present disclosure are not affected by variations in the illumination and detection of the imaging systems as well as the background ambient room light as follows: The measured spectral intensity $I_m(\lambda)$ reflected from the inner eyelid in a given location of (x, y) is expressed as a function of the wavelength $\lambda$:

$$I_m(\lambda) = L(\lambda)C(\lambda)D(\lambda)r(\lambda) \quad (1)$$

where L ($\lambda$) is the spectral shape of the illumination light source, $C(\lambda)$ is the spectral response of all optical components in the imaging system (e.g. lenses and diffraction grating), $D(\lambda)$ is the spectral response of the detector (e.g. mono imaging sensor or RGB imaging sensor in the image-guided hyperspectral linescanning system), and $r(\lambda)$ is the true spectral intensity reflected from the inner eyelid. First, to compensate for the system response (i.e. $L(\lambda)C(\lambda)D(\lambda)$), we use the reference reflectance standards that have a reflectivity of 99% in the visible range. $I_m(\lambda)$ is normalized by the reflectance measurement $I_{reference}(\lambda)$ of the diffuse reflectance standard in which $r_{reference}(\lambda)=0.99$ in the visible range $$r(\lambda) = \frac{I_m(\lambda)}{I_{reference}(\lambda)} \quad (2)$$

Second, to remove the ambient stray and background light $I_{background}(\lambda)$, two measurements are acquired with the external light source (i.e., white-light LED ring illuminator of the custom-built dual imaging system) on and off. The measurements are repeated without the sample while the illumination is kept on. Finally, $r(\lambda)$ is calculated by subtracting $I_{background}(\lambda)$ from each measurement such that:

$$r(\lambda) = \frac{I_m(\lambda) - I_{backgroud}(\lambda)}{I_{reference}(\lambda) - I_{backgroud}(\lambda)} \quad (3)$$

This systematic and rigorous data acquisition procedure serves as the foundation for developing a reliable VHI transformation matrix and a universal blood Hgb computation algorithm. It should be noted that the built-in data acquisition step to factor out the contributions of room light conditions provides a unique advantage to generate this reliable blood Hgb calculation.

Figure 2G:
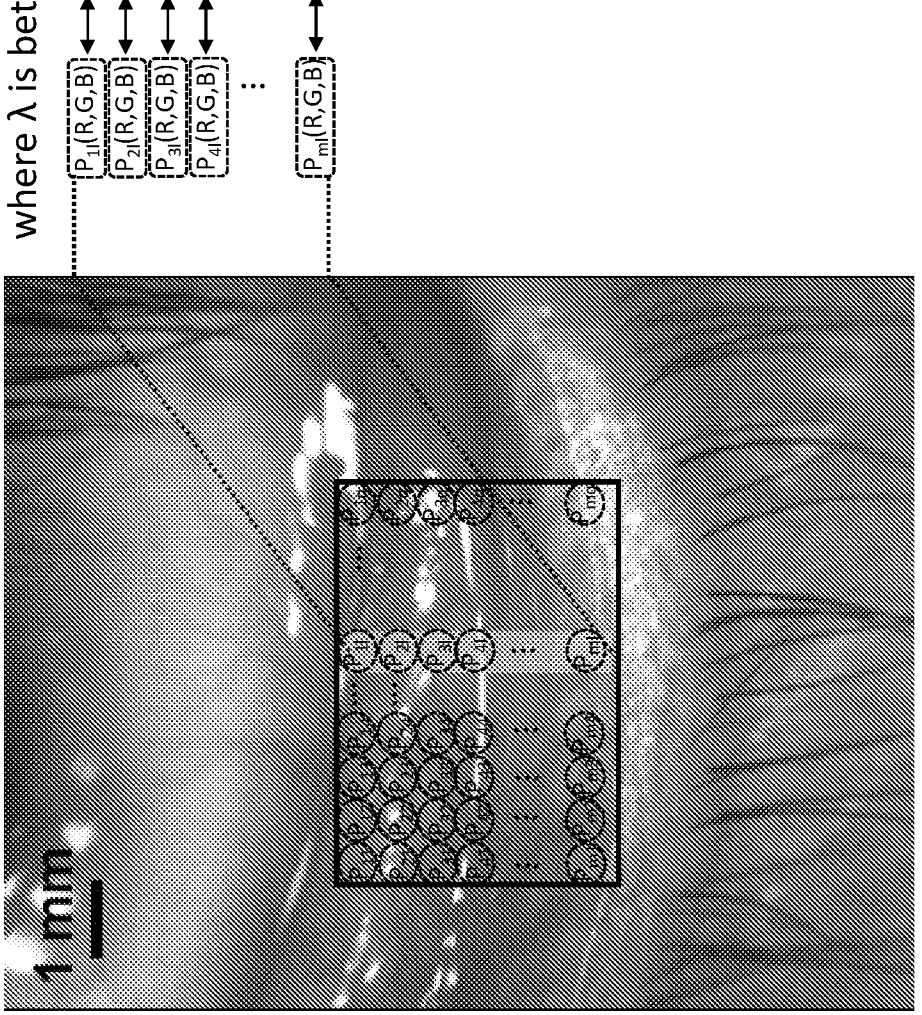
FIG. 2*g* is a photograph of the inner eyelid, with a frame of pixels shown thereon.

To better understand this approach, reference is made to FIG. 2*g* which is a photograph of the inner eyelid, with a frame of pixels shown thereon. The frame is an RGB 2-dimensional frame and includes pixels in the X-direction and the Y-direction. The corner pixel is shown as $P_1$. The first row of pixels includes pixels $P_{11}$, $P_{12}$, $P_{13}$, $P_{14}$, . . . $P_{1l}$, . . . and $P_{1q}$. The second row includes pixels $P_{21}$, $P_{22}$, $P_{23}$, $P_{24}$, . . . $P_{2l}$, . . . and $P_{2q}$, until the last row which includes pixels $P_{m1}$, $P_{m2}$, $P_{m3}$, $P_{m4}$, . . . $P_{ml}$, . . . and $P_{mq}$. The first column of pixels includes pixels $P_{11}$, $P_{21}$, $P_{31}$, $P_{41}$, . . .

$P_{m1}$. The second column includes pixels $P_{12}$, $P_{22}$, $P_{32}$, $P_{42}$, . . . $P_{m2}$. The last column includes pixels $P_{1q}$, $P_{2q}$, $P_{3q}$, $P_{4q}$, . . . $P_{mq}$. The $l^{th}$ column which happens to be the column which is coincident with the column with the hyperspectral data (linescan) includes pixels $P_{11}$, $P_{21}$, $P_{31}$, $P_{41}$, . . . $P_{m1}$ (note the second index in each pixel is lowercase L (i.e., "l" and not one ("1")). This column provides the aforementioned limited hyperspectral data. Concentrating on the $l^{th}$ column, each pixel (i.e., $P_{11}$, $P_{21}$, $P_{31}$, $P_{41}$, . . . $P_{ml}$) having an RGB intensity can be paired to the corresponding hyperspectral pixel with a corresponding wavelength data (i.e., $\lambda_1$, $\lambda_2$, $\lambda_3$, $\lambda_4$, . . . $\lambda_m$) where $\lambda$ represents a discretized wavelength between a first wavelength (e.g., 450 nm) and a second wavelength (e.g., 679 nm). That is each hyperspectral pixel is represented by a spectrum bounded between the lower and upper bounds. For a discretized spectrum, the number of wavelengths is identified as N. Therefore, for pixel $P_{11}$, one can correlate the RGB intensity of the pixel $P_{11}$ to the spectrum obtained from the hyperspectral imaging of the same pixel (obtained at preferably the same time with different cameras). A transformation matrix can be derived from this correlation that can then be applied to other pixels and their associated RGB intensities in order to derive corresponding spectra of those other pixels.

Figure 2H:
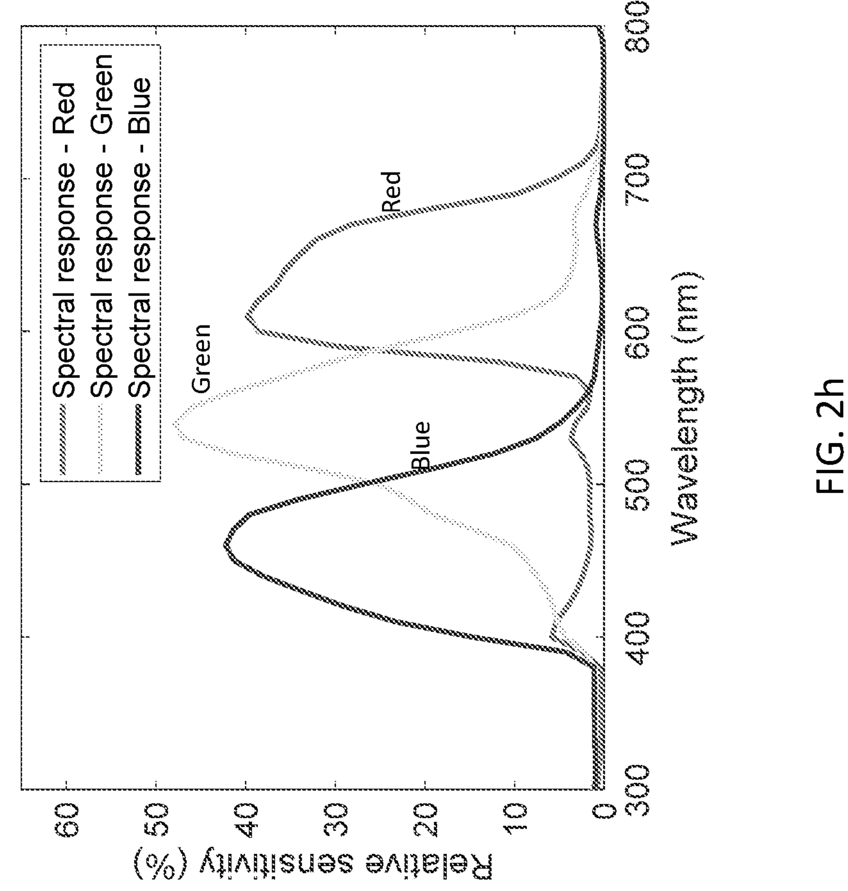
FIG. 2*h* is a graph of relative sensitivity (%) vs wavelength in (nm) for red, green, and blue spectral responses of a camera.
Figure 3:
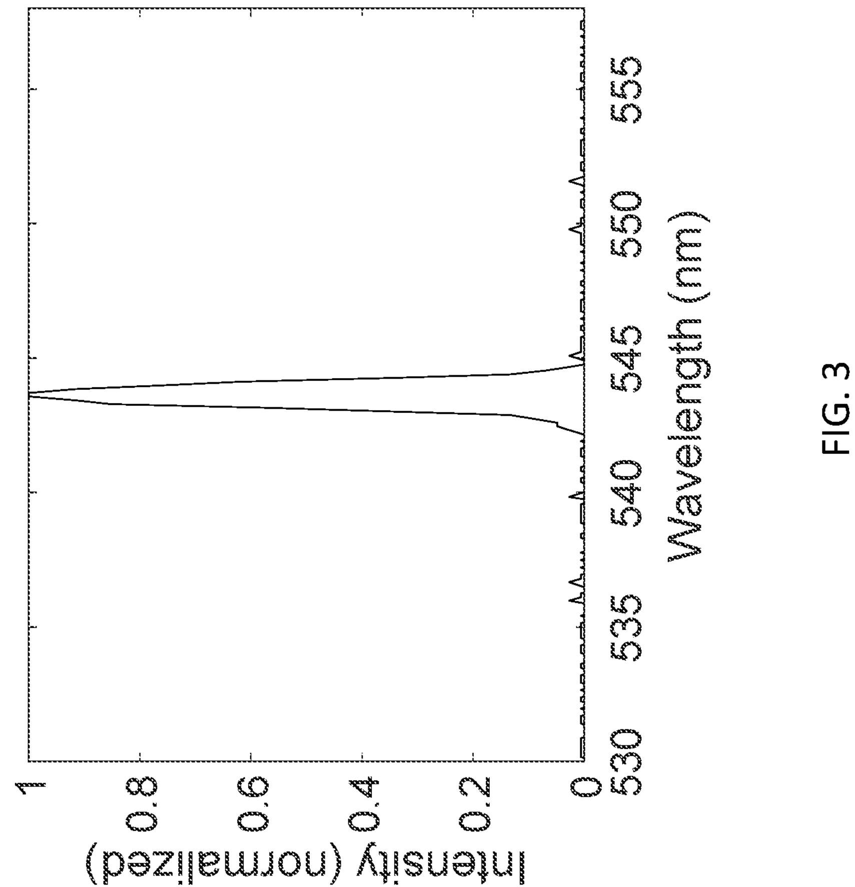
FIG. 3 is a graph of normalized intensity vs. wavelength in nm of full width at half maximum (FWHM) of a HeNe laser.
Figure 4:
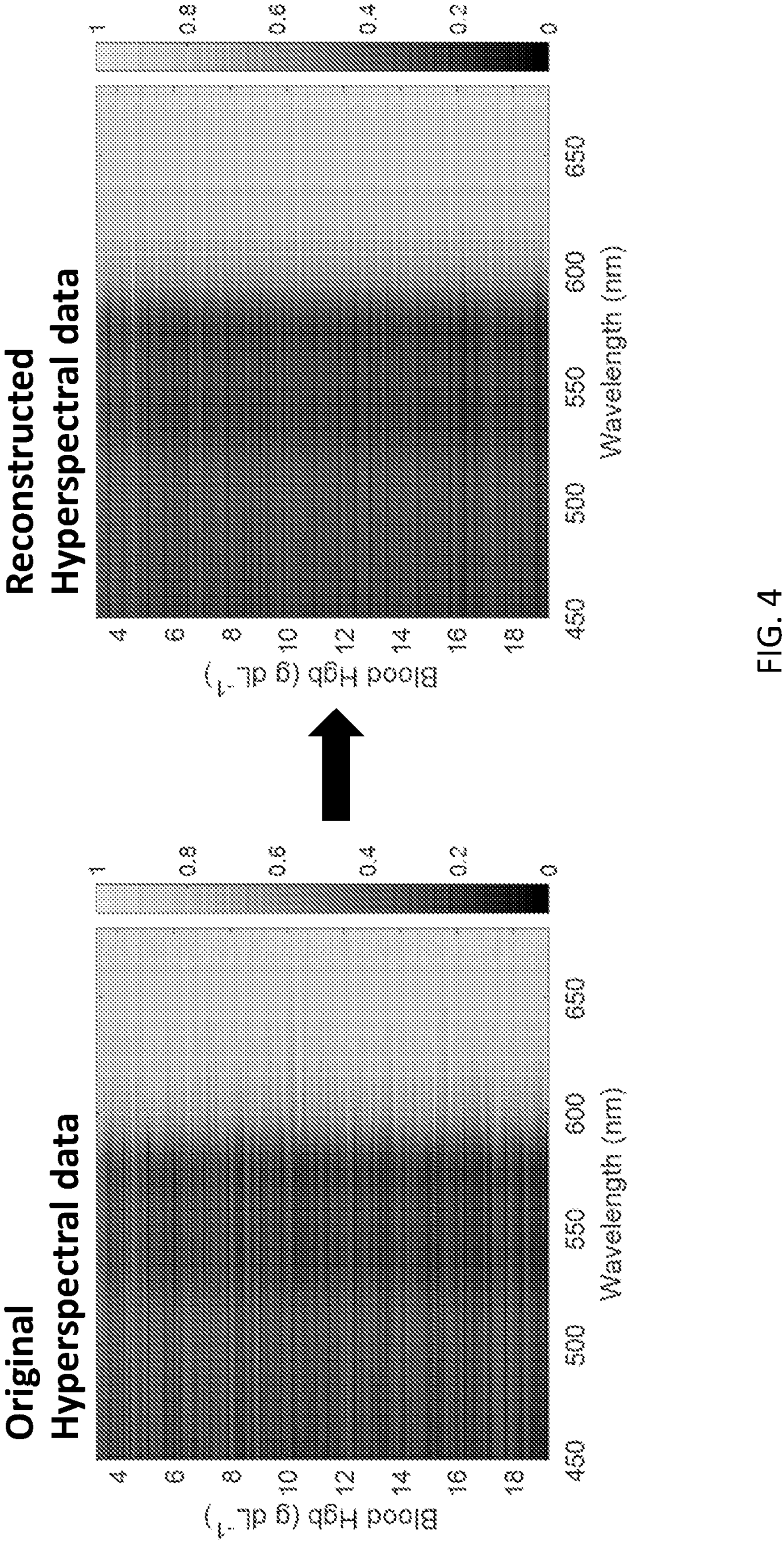
FIG. 4 are graphs of blood hemoglobin (HGb) in g $dL^{-1}$ vs. wavelength in nm showing comparison between a hyperspectral dataset (acquired by the image-guided hyperspectral system) and the algorithm-reconstructed hyperspectral datasets (based on an RGB image) according to the algorithm of the present disclosure for various levels of blood Hgb levels.

In the case of VHI, a mathematical reconstruction of the full spectral information from an RGB image taken by a conventional camera (i.e. three-color information from Red, Green, and Blue channels) is generated, according to the present disclosure. Referring to FIG. 3, the spectral resolution ($\Delta\lambda$=1 nm) of the system by measuring full width at half maximum (FWHM) of a HeNe laser is provided. The mathematical relationship between the full spectrum and the RGB intensity is described as $$x = Sr + e \quad (4)$$

where x is a vector corresponding to the reflection intensity in each R, G, and B channel, S is a matrix of the RGB spectral response functions of the three-color sensor, r is a vector of the spectral intensity reflected from the inner eyelid, and e is a vector of the system noise. In our case, the hyperspectral reconstruction from the RGB signal is an inverse problem such that the number of actual measurements (i.e. three-color information) is less than the dimensionality of the full spectrum with $\lambda=\lambda_1, \lambda_2, \ldots, \lambda_N$. Given the relatively limited sample size, we took advantage of fixed-design linear regression with polynomial features to reliably reconstruct the full spectral information $r(\lambda_1, \lambda_2, \ldots, \lambda_N)$ from the RGB signals x(R, G, B) of the three-color RGB sensor, as shown in FIG. 4; wherein a comparison between the original hyperspectral dataset (acquired by the image-guided hyperspectral system) and the VHI-reconstructed hyperspectral datasets (based on an RGB image) are provided for various levels of blood Hgb levels. The differences in the wavelength range between 450 and 575 nm are generally higher, because the distinct Hgb absorption is present in this range. To better demonstrate the construction of the transformation matrix, reference is made to FIG. 1*d*. First, the method 150 describes the measured RGB intensity as provided in a block 154:

$$x_{3\times1} = S_{3\times N} r_{N\times1} + e_{3\times1} \quad (5\text{-}1)$$

where x is a 3×1 vector corresponding to the reflection intensity in each R, G, and B channel (e.g., pixel $P_{11}$, is identified by $x_{3\times1}$ which is a 3×1 matrix with each row associated with an RGB channel output, i.e., the first row represents the R value, the second row represents the G value, and the third row represents the B value), S is a 3×N matrix of the RGB spectral response functions of the 3-color sensor, i.e. built-in camera (S represent the discretized versions of the spectra for each RGB channel, as shown in FIG. 2*h*, in the form of a matrix, i.e., the first row of S is the spectrum for relative intensity of the R channel output of the sensor over discretized range bounded between a lower and upper range, the second row of S is the spectrum for relative intensity of the G channel output of the sensor over discretized range bounded between the lower and upper range, the third row of S is the spectrum for relative intensity of the B channel output of the sensor over discretized range bounded between the lower and upper range), r is an N×1 vector that has the spectral reflection intensity (that is r is the spectrum over discretized range bounded between the lower and upper range of the pixel from the hyperspectral image)—in our case, $r(\lambda=\lambda_1, \lambda_2, \ldots, \lambda_N)$ is discretized from 450 nm to 679 nm with a spectral interval of 1 nm, and e is a 3×1 vector of the system noise with zero mean. The hyperspectral reconstruction from the RGB signal is to obtain $[S_{3\times N}]^{-1}$. However, this inverse calculation is an underdetermined problem since N>3.

To solve this underdetermined problem, we formulate fixed-design linear regression with polynomial features of the three-color information to infer the spectral information r from the RGB signals x. We take advantage of multiple collections of the hyperspectral reflection dataset (acquired by the image-guided hyperspectral line-scanning system) and the RGB dataset (acquired by the RGB camera), respectively. $X_{3\times m}$ and $R_{N\times m}$ are formed by adding $x_{3\times1}$ and $r_{N\times1}$ from m different measurements. Referring to FIG. 2*g*, while the aforementioned underdetermined problem as initially described with respect to pixel $P_{11}$, there are m pixels in the $l^{th}$ column of the frame. Therefore, other pixels in equation (5-1) can be used to numerically solve for $[S_{3\times N}]^{-1}$ in an alternative manner, as provided in a block 156 of FIG. 1*d*. The relationship in Equation (5-1) is described as:

$$X_{3\times m} = S_{3\times N} R_{N\times m} \tag{5-2}$$

which can be expressed as:

$$R_{N\times m} = T_{N\times 3} X_{3\times m} \tag{5-3}$$

where the transformation (or extrapolation) matrix is $T_{N\times3}=[S_{3\times N}]^{-1}$, as provided in a block 158 in FIG. 1*d*. If Equation (5-3) is solved for the unknown $T_{N\times3}$, then $T_{N\times3}$ can be used to convert the RGB dataset into the hyperspectral reflection dataset, as provided in a block 160 in FIG. 1*d*.

Next, each three-color sensor model in different cameras has unique RGB spectral responses with spectral overlaps among the R, G, and B channels (also known as the sensitivity function of the camera), as discussed above with reference to FIG. 2*h*. To effectively incorporate the RGB spectral response of the camera, we expand $X_{3\times m}$ to $\hat{X}_{p\times m}$ for maximizing the accuracy of the hyperspectral reconstruction such that:

$$R_{N\times m} = \hat{T}_{N\times p} \hat{X}_{p\times m} \tag{5-4}$$

here $\hat{X}_{p\times m}$ can be expressed explicitly such that:

$$\hat{X}_{p\times m} = \begin{bmatrix} R_1 & G_1 & B_1 & \ldots & R_1^i & G_1^i & B_1^i & R_1G_1 & G_1B_1 & B_1R_1 & \ldots & (R_1G_1)^j & (G_1B_1)^j & (B_1R_1)^j & R_1G_1B_1 & \ldots & (R_1G_1B_1)^j \\ \vdots & \vdots & \vdots & \vdots & \vdots & \vdots & \vdots & \vdots & \vdots & \vdots & \vdots & \vdots & \vdots & \vdots & \vdots & \vdots & \vdots \\ R_m & G_m & B_m & \ldots & R_m^i & G_m^i & B_m^i & R_mG_m & G_mB_m & B_mR_m & \ldots & (R_mG_m)^j & (G_mB_m)^r & (B_mR_m)^j & R_mG_mB_m & \ldots & (R_mG_mB_m)^j \end{bmatrix}^T \tag{5-5}$$

where the exact powers of i and j of the single and cross terms are uniquely determined for a specific three-color sensor model, by checking the error between the reconstructed hyperspectral data and the original data.

Next, the inverse of the expanded transformation matrix $\hat{T}$ in Equation (5-4) can be considered to be the minimum-norm-residual solution to $R=\hat{T}\hat{X}$. Typically, this inverse problem is to solve a least-squares problem. We take use of QR decomposition, in particular the QR solver. After QR factorization is applied to $\hat{X}$, $\hat{T}$ is estimated by minimizing the sum of the squares of the elements of $R-\hat{T}\hat{X}$ and is selected such that the number of nonzero entries in $\hat{T}$ is minimized. Overall, the computation of the transformation (extrapolation) matrix establishes VHI, eliminating a need of bulky dispersion hardware components (e.g. spectrometer, spectrograph, mechanical filter wheel, or liquid crystal tunable filter).

We validated the performance of the RGB-assisted VHI as shown FIGS. 5*a*, 5*b*, and 5*c*. The line #1 (shown in FIG. 5*a*) was used to construct the transformation matrix that generates hyperspectral data from RGB data. The transformation matrix was applied to the RGB data of Line #2 to generate a hyperspectral linescan of Line #2 (see FIGS. 5*a*, 5*b*, and 5*c*). This extrapolated data is compared with a measured hyperspectral linescan of Line #2 by moving the systems. The reconstructed data is in excellent agreement with the original data. When the hyperspectral data were averaged over the line scanning direction into a spectrum, the reconstructed spectrum is also in excellent agreement with the original one.

Figure 6:
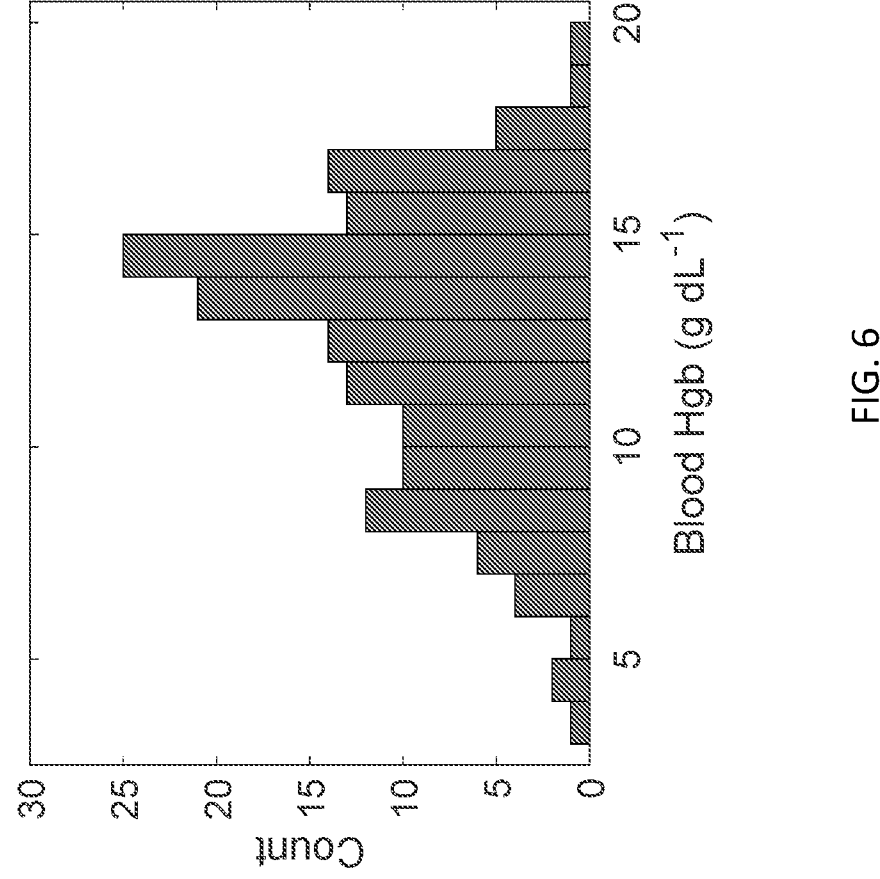
FIG. 6 is histogram which summarizes the blood Hgb values of a total of 153 individuals that were used for spectroscopic and blood Hgb reconstruction measurements using the algorithm of the present disclosure.

In order to make comparison with clinical data, reference is made to FIG. 6 which summarizes the blood Hgb values of a total of 153 individuals that were used for spectroscopic and VHI blood Hgb measurements. The study covers a wide range of Hgb values from 3.3 to 19.2 g $dL^{-1}$. We conducted a clinical study within the facilities overseen by the accepted authorities. We enrolled patients who were referred for complete blood count (CBC) tests. For all individuals enrolled in the study, we collected hyperspectral data and RGB images from the palpebral conjunctiva (i.e. inner eyelid) using an image-guided hyperspectral line-scanning system. As the 'gold standard' clinical laboratory measurements, blood Hgb levels were measured in an Accredited Clinical Laboratory using a commercial hematology analyzer (BECKMAN COULTER AcT 5diff auto, BECKMAN COULTER, INC.). For developing the blood Hgb quantification algorithm, we randomly selected 138 individuals (78 females and 60 males) to use as a preliminary (training) dataset. The average Hgb level is 12.65 g $dL^{-1}$ with a standard deviation (SD) of 3.11 g $dL^{-1}$ and the average age is 37.78 years with SD of 16.38 years. As a new masked (testing) dataset, we employed the rest of 15 individuals (12 females and 3 males) not included in the preliminary dataset. The average Hgb level is 11.06 g $dL^{-1}$ with SD of 3.62 g $dL^{-1}$. The average age is 39.13 years with SD of 17.30 years.

We now describe the partial least square regression (PLSR) to estimate a blood Hgb level from the hyperspectral information averaged from the entire inner eyelid. We built a model for computing blood Hgb content from the hyperspectral reflection data averaged over the inner eyelid. Analytical model-based Hgb prediction methods are often used, because Hgb has distinct spectral signatures (e.g. Soret and Q bands) in the visible range. However, such model-based approaches often require a priori information on all possible light absorbers in tissue for reliable Hgb quantification. Thus, we made use of PLSR, which can be used to model relationships among measured variables (i.e. predictors) and response variables (i.e. outcomes). Because PLSR transforms high-dimensional measured variables onto a reduced space of latent variables, it is highly beneficial to examine the significance of individual measured variables by eliminating insignificant variables. While PLSR is based on the extraction of principal components, it incorporates variations of both predictor and outcome variables simultaneously, enhancing the prediction performance. Similar to principal component analysis, it is critical to determine an optimal number of components in PLSR, as a greater number of components better captures variations in the predictor and outcome variables, thus lowering the prediction error. The determination of an optimal number of principal components in ten-fold cross-validation of partial least squares regression (PLSR) is thus performed. In particular, as the number of partial least squares (PLS) components increases, the percentage variance in the true Hgb values (outcome variable) increases, while the mean squared prediction error has minimal values for 18 components. These numbers of PLS components contribute to appropriate representation of variations in the spectroscopic and laboratory blood Hgb values simultaneously, thus making its prediction errors lower. As a result, 18 PLS components are selected and used in the Hgb prediction model. We can select an optimal number of components using cross-validation in a conservative manner as follows: The original dataset was randomly grouped into sub-datasets with the same sample size. One sub-dataset was not used for training the model and was retained as a validation dataset for testing the model. After this process was repeated, the different validations were averaged. The main advantage of such a cross-validation is that all of the datasets were incorporated to determine the optimal number of principal components, given the limited number of individuals. Although the use of PLSR often avoids overfitting when the number of predictors is larger than the sample size, it is also important to evaluate the ability for predicting Hgb levels from a completely new dataset after the model is established properly. Thus, we defined the two datasets for training and testing the blood Hgb model without reutilization of data from the same individuals.

Based on the aforementioned information, a hyperspectral/imaging data processing and statistical analysis is now provided. For data processing and algorithm development, we computed the hyperspectral and RGB data and developed the blood Hgb prediction model and the VHI algorithm using MATLAB (MATLAB R2018b, The MathWorks, Inc.). For statistical analyses, we evaluated multiple linear regression, linear correlations, and intra-class correlations using STATA (STATA 14.2, STATACORP LLC). We conducted Bland-Altman analyses to compare the blood Hgb measurements as non-parametric methods. The bias is defined by the mean of the differences between the hyperspectral (or VHI) and central laboratory blood Hgb measurements ($d=y^{VHI}-y^{central}$):

$$\text{Bias} = \bar{d} = \frac{1}{n}\sum\nolimits_{k=1}^{n} d_k. \tag{6}$$

The 95% limits of agreement (LOA) is defined by a 95% prediction interval of the standard deviation:

$$LOA = \bar{d} \pm 1.96\sqrt{\frac{1}{n-1}\sum\nolimits_{k=1}^{n} = (d_k - \bar{d})}. \tag{7}$$

Several patients have multiple disorders. Types of cancer include Kaposi sarcoma, breast cancer, skin cancer, and Hodgkin's lymphoma. SD means standard deviation.

TABLE 1

Patient characteristics

| Disorder | Number of patients |
| --- | --- |
| Cancer | 45 |
| HIV | 46 |
| Tuberculosis | 8 |
| Sickle cell disease | 19 |
| Acute kidney failure | 1 |
| Heart failure | 4 |
| Malaria | 1 |
| Anemia | 3 |
| Immune thrombocytopenic purpura | 1 |
| No major disease | 25 |
| Dataset | Average Hgb (g $dL^{-1}$) |
| Preliminary (training) dataset (n = 138) | 12.65 (SD = 3.11) |
| Masked (testing) dataset (n = 15) | 11.06 (SD = 3.62) |

Using the system shown in FIG. 2*a* which includes a hyperspectral imaging system with an integrated and cooperative RGB camera, we conducted imaging sessions which results are provided in FIG. 6 and referred to above. In particular, the guiding camera allows us to pinpoint the exact location of one or more hyperspectral line-scanning in the inner eyelid, see FIG. 2*b*. The subject sits and places his/her chin on the chinrest and pulls down the eyelid for imaging when instructed. The white-light LED is illuminated on the inner eyelid, ensuring minimal light exposure to the eye. The guiding image panel shows a guide line corresponding to the location of the spectrograph slit, which is positioned vertically to acquire a hyperspectral line-scan dataset over the entire inner eyelid from top to bottom, see FIGS. 2*c*-2*f*. The image-guided hyperspectral line-scanning system acquires a snapshot of spatial-spectral information only for three seconds. To factor out the ambient room light, two measurements are conducted with the white-light LED on and off. To compensate for the system spectral response, the reflectance standard is used as a reference measurement.

Figure 7:
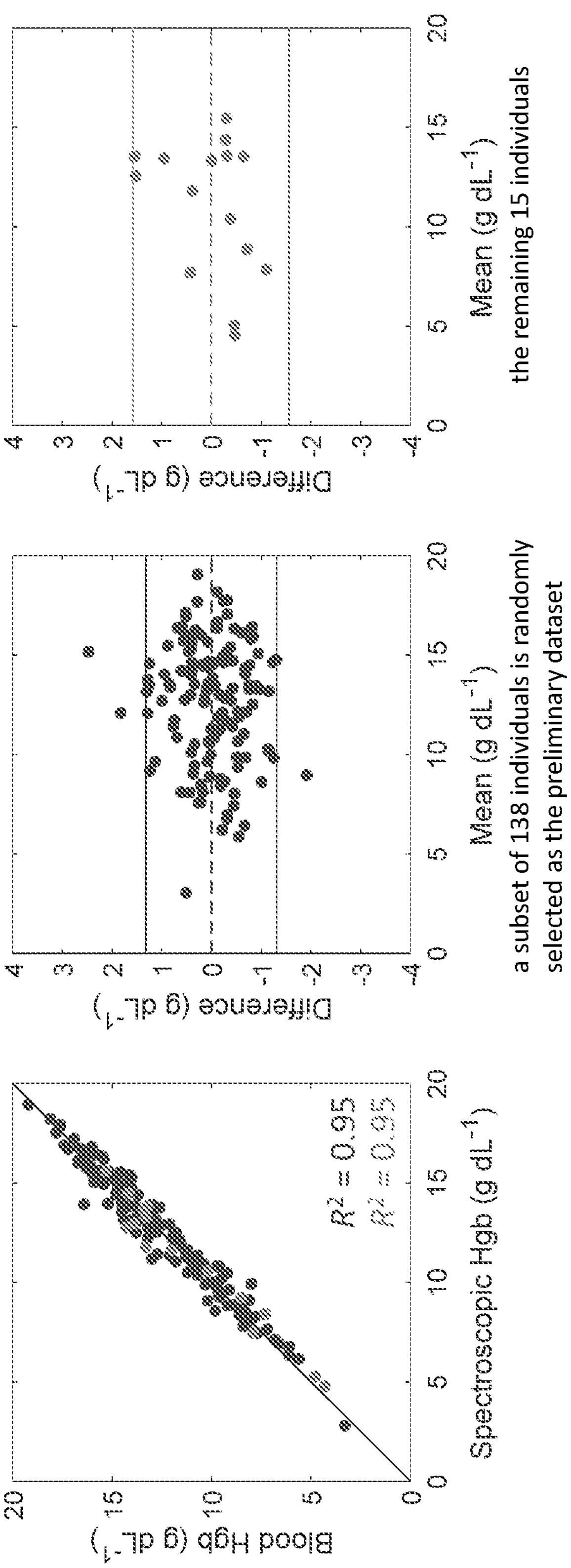
FIG. 7 is a collection of graphs of a linear correlation between the computed blood Hgb content and the laboratory blood Hgb levels and differences in blood hemoglobin in g $dL^{-1}$ for one subset of the population of individuals (138) used as training data as well as a second population of individuals (15) used as testing data.

A spectrum reflected from the inner eyelid directly acquired by the image-guided hyperspectral line-scanning system allows us to build a blood Hgb extraction model for predicting actual blood Hgb content. First, we constructed a prediction model of blood Hgb levels using the preliminary (training) dataset of 138 individuals, using PLSR. In our case, a reflection spectrum $r(\lambda)$ has multicollinearity due to the large number of wavelengths ($\lambda=\lambda_1, \lambda_2, \ldots, \lambda_N$) and only a handful of the underlying latent variables are responsible for capturing the most variations in the predictor variables. Using ten-fold cross-validation, we determined 18 principal components as an optimal number of PLSR components for the blood Hgb prediction model. The results are shown in FIG. 7. In FIG. 7, a linear correlation between the computed blood Hgb content and the laboratory blood Hgb levels (i.e. the gold standard) is provided which shows an excellent $R^2$ value of 0.95 for the preliminary dataset. When the Bland-Altman analysis is used to compare the two blood Hgb measurements, the 95% limits of agreement (LOA) exclude three out of 138 (2.17% outside LOA) with bias of 0 g $dL^{-1}$. Second, we applied the same Hgb prediction model to the separate testing dataset of 15 individuals. FIG. 7 shows that LOA includes 15 computed blood Hgb values with bias of 0.01 g $dL^{-1}$. In addition, an excellent $R^2$ value of 0.95 for the testing dataset supports the prediction model. Both preliminary and testing results clearly support the underlying idea that the full hyperspectral information of the inner eyelid can be used for accurately and precisely extracting actual Hgb count in the blood, noninvasively.

In further description of FIG. 7, to strengthen the validation of the blood Hgb prediction, two separate preliminary and masked testing datasets are used without reuse of individuals; a subset of 138 individuals is randomly selected as the preliminary dataset and the remaining 15 individuals is used to test the blood Hgb model. The Bland-Altman analyses compare the computed blood Hgb measurements with the laboratory blood Hgb test results, showing 95% limits of agreement (LOA) and bias in each system. With reference to FIG. 7, spectroscopic blood Hgb measurements using the image-guided hyperspectral line-scanning system show the excellent performance with narrow LOA of [−1.31, 1.31 g $dL^{-1}$] with bias of 0 g $dL^{-1}$ for the preliminary dataset. The testing dataset also supports a consistent yet low error in the blood Hgb measurements for the testing dataset. Only three out of 138 data points fall outside LOA for the preliminary dataset and none out of 15 for the testing dataset, indicating a consistent yet low error in the blood Hgb measurements.

Those having ordinary skill in the art will recognize that numerous modifications can be made to the specific implementations described above. The implementations should not be limited to the particular limitations described. Other implementations may be possible.

The invention claimed is:

1. A system for generating hyperspectral image data for measuring blood hemoglobin, comprising:

an optical imaging device with a red-green-blue (RGB) sensor adapted to acquire an RGB image representing an entire region of interest having a predetermined size of a plurality of RGB pixels thereby generating an RGB dataset;

a linescan spectral imaging device adapted to acquire one or more hyperspectral linescans from a subregion of the entire region of interest, wherein the subregion is substantially smaller than the entire region of interest, thereby generating one or more hyperspectral linescan datasets;

a processor adapted to:

co-locate a plurality of RGB pixels in the RGB dataset vs. a corresponding plurality of hyperspectral pixels of in the one or more hyperspectral linescan datasets representing the subregion, establish a transformation matrix utilizing the plurality of co-located RGB and hyperspectral pixels, the transformation matrix adapted to convert the RGB dataset into a hyperspectral dataset of the subregion, apply the transformation matrix to the RGB dataset to thereby generate the a hyperspectral dataset for the entire region of interest, and analyze the generated hyperspectral image dataset to determine the biochemical compositions.

2. The system of claim 1, wherein each of the plurality of RGB co-located pixels is associated with a 3×1 RGB value matrix.

3. The system of claim 2, wherein each of the co-located plurality of hyperspectral pixels is associated with an N×1 spectrum matrix, where N represents discretized spectra between a lower bound and an upper bound.

4. The system of claim 3, wherein the lower and upper bounds are determined by spectral ranges of the RGB sensor.

5. The system of claim 1, wherein the transformation matrix is a pseudo inverse of an RGB response function matrix of the RGB sensor.

6. The system of claim 5, wherein inverse of the transformation matrix is determined numerically by using RGB and spectral data from a subset of the co-located plurality of RGB and hyperspectral pixels, corresponding to the subregion.

7. The system of claim 1, wherein the entire region of interest includes conjunctiva.

8. The system of claim 1, wherein the hyperspectral analysis includes a partial least square regression statistical modeling technique to first build a model from a training set of a first hyperspectral dataset vs. the biochemical compositions and then apply the model to the hyperspectral dataset for the entire region of interest.

9. A method for generating hyperspectral imaging image data for measuring blood hemoglobin, comprising:

obtaining a red-green-blue (RGB) image using an optical imaging device with an RGB sensor representing an entire region of interest having a predetermined size corresponding to a matrix of a first plurality of RGB pixels from a scene thereby generating an RGB dataset;

obtaining one or more hyperspectral linescans using a linescan spectral imaging device from a subregion of the entire region of interest, wherein the subregion is substantially smaller than the entire region of interest, thereby generating one or more hyperspectral linescan datasets;

co-locating a plurality of RGB pixels in the RGB dataset vs. a corresponding plurality of pixels in the one or more hyperspectral linescan datasets representing the subregion;

establishing a transformation matrix utilizing the plurality of co-located RGB and hyperspectral pixels, the transformation matrix adapted to convert the RGB dataset into a hyperspectral dataset of the subregion;

applying the transformation matrix to the RGB dataset to thereby generate a hyperspectral dataset for the entire region of interest; and analyzing the generated hyperspectral image dataset to determine blood hemoglobin.

10. The method of claim 9, wherein each of the plurality of RGB co-located pixels is associated with a 3×1 RGB value matrix.

11. The method of claim 10, wherein each of the co-located plurality of hyperspectral pixels is associated with an N×1 spectrum matrix, where N represents discretized spectra between a lower bound and an upper bound.

12. The method of claim 11, wherein the lower and upper bounds are determined by spectral ranges of the RGB sensor.

13. The method of claim 9, wherein the transformation matrix is a pseudo inverse of an RGB response function matrix of the RGB sensor.

14. The method of claim 13, wherein the inverse of the transformation matrix is determined numerically by using RGB and spectral data from a subset of the co-located plurality of RGB and hyperspectral pixels, corresponding to the subregion.

15. The method of claim 9, wherein the entire region of interest includes conjunctiva.

16. The method of claim 9, wherein the hyperspectral analysis includes a partial least square regression statistical modeling technique to first build a model from a training set of a first hyperspectral dataset vs. the biochemical compositions and then apply the model to the hyperspectral dataset for the entire region of interest.

* * * * *